(12) United States Patent
Hirahara et al.

(10) Patent No.: US 9,132,076 B2
(45) Date of Patent: *Sep. 15, 2015

(54) CLEANING AGENT COMPOSITION

(75) Inventors: Mayuko Hirahara, Bunkyo-ku (JP); Izumi Katsuta, Bunkyo-ku (JP); Hiroki Mizushima, Wakayama (JP); Azusa Kasuga, Sumida-ku (JP); Eiji Terada, Sumida-ku (JP)

(73) Assignee: KAO CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/115,521

(22) PCT Filed: May 1, 2012

(86) PCT No.: PCT/JP2012/061553

§ 371 (c)(1),
(2), (4) Date: Nov. 4, 2013

(87) PCT Pub. No.: WO2012/150709

PCT Pub. Date: Nov. 8, 2012

(65) Prior Publication Data

US 2014/0144456 A1 May 29, 2014

(30) Foreign Application Priority Data

May 2, 2011 (JP) ................................ 2011-102878
May 2, 2011 (JP) ................................ 2011-103053

(51) Int. Cl.

| | | |
|---|---|---|
| *A61K 8/73* | (2006.01) | |
| *A61K 8/37* | (2006.01) | |
| *A61K 8/46* | (2006.01) | |
| *A61Q 5/02* | (2006.01) | |
| *A61Q 19/10* | (2006.01) | |
| *C08B 11/193* | (2006.01) | |
| *C08L 1/26* | (2006.01) | |
| *C08L 1/28* | (2006.01) | |
| *C08B 1/06* | (2006.01) | |
| *C08B 1/08* | (2006.01) | |
| *C08B 11/08* | (2006.01) | |
| *C08B 11/145* | (2006.01) | |

(52) U.S. Cl.
CPC ................ *A61K 8/731* (2013.01); *A61K 8/375* (2013.01); *A61K 8/463* (2013.01); *A61Q 5/02* (2013.01); *A61Q 19/10* (2013.01); *C08B 1/06* (2013.01); *C08B 1/08* (2013.01); *C08B 11/08* (2013.01); *C08B 11/145* (2013.01); *C08B 11/193* (2013.01); *C08L 1/26* (2013.01); *C08L 1/284* (2013.01); *C08L 1/288* (2013.01)

(58) Field of Classification Search
None
See application file for complete search history.

(56) References Cited

U.S. PATENT DOCUMENTS

| | | | |
|---|---|---|---|
| 3,816,616 A | 6/1974 | Anguillo et al. | |
| 6,221,816 B1 | 4/2001 | Kasuga et al. | |
| 7,960,327 B2 * | 6/2011 | Uchiyama et al. | ............ 510/130 |
| 2005/0159331 A1 | 7/2005 | Tamura et al. | |
| 2006/0051308 A1 | 3/2006 | Terada | |
| 2006/0160714 A1 | 7/2006 | Terada | |
| 2007/0111922 A1 | 5/2007 | Tamura et al. | |
| 2007/0269398 A1 | 11/2007 | Terada | |
| 2009/0023623 A1 | 1/2009 | Yamamoto et al. | |
| 2009/0253603 A1 | 10/2009 | Uchiyama et al. | |
| 2011/0212880 A1 | 9/2011 | Inoue et al. | |
| 2012/0015894 A1 | 1/2012 | Terada | |
| 2012/0214985 A1 | 8/2012 | Takai et al. | |
| 2012/0230934 A1 | 9/2012 | Doi et al. | |
| 2014/0094423 A1 | 4/2014 | Terada | |

FOREIGN PATENT DOCUMENTS

| | | |
|---|---|---|
| CN | 101484568 A | 7/2009 |
| EP | 1 859 780 A1 | 11/2007 |
| JP | 59 42681 | 10/1984 |
| JP | 5-112795 A | 5/1993 |
| JP | 5 148123 | 6/1993 |

(Continued)

OTHER PUBLICATIONS

Extended European Search Report issued on Nov. 6, 2014 in Patent Application No. 12780039.9.
International Search Report Issued Aug. 14, 2012 in PCT/JP12/61553 Filed May 1, 2012.
U.S. Appl. No. 14/114,544, filed Oct. 29, 2013, Hirahara, et al.
U.S. Appl. No. 14/115,193, filed Nov. 1, 2013, Hirahara, et al.
New cosmetics studies, Nanzando, Second Edition, Jan. 18, 2001, pp. 441-445 (with translation by computer).

*Primary Examiner* — Jyothsna Venkat
(74) *Attorney, Agent, or Firm* — Oblon, McClelland, Maier & Neustadt, L.L.P.

(57) ABSTRACT

A cleansing composition comprising (A) an anion surfactant, (B) a glyceryl ether having an alkyl group or alkenyl group with from 4 to 12 carbon atoms, (C) a cationized hydroxypropyl cellulose represented by the following formula (1) wherein $R^1$, $R^2$ and $R^3$ each independently represent a substituent having a cationized ethyleneoxy group and a propyleneoxy group and n represents a number of from 20 to 5000, which represents an average polymerization degree of anhydroglucose, and wherein the substitution degree of the cationized ethyleneoxy group is from 0.01 to 3, and the substitution degree of the propyleneoxy group is from 0.01 to 5, and (D) water.

(1)

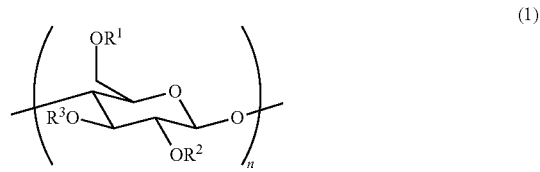

22 Claims, No Drawings

(56) References Cited

FOREIGN PATENT DOCUMENTS

| | | |
|---|---|---|
| JP | 2001-107096 A | 4/2001 |
| JP | 2001 107097 | 4/2001 |
| JP | 2001 115187 | 4/2001 |
| JP | 2004-67640 A | 3/2004 |
| JP | 2005 306843 | 11/2005 |
| JP | 2006-182728 A | 7/2006 |
| JP | 2007 308450 | 11/2007 |
| JP | 2008-31468 A | 2/2008 |
| JP | 2008-156274 A | 7/2008 |
| JP | 2008 308492 | 12/2008 |
| JP | 2009-062546 A | 3/2009 |
| JP | 2010-70529 A | 4/2010 |
| JP | 2010-150315 A | 7/2010 |
| JP | 2010-235523 A | 10/2010 |
| WO | WO 2008004342 * | 1/2008 |
| WO | WO 2010/113446 A1 | 10/2010 |
| WO | 2011 059063 | 5/2011 |
| WO | 2012 091072 | 7/2012 |

* cited by examiner

CLEANING AGENT COMPOSITION

FIELD OF THE INVENTION

The present invention relates to a cleansing composition.

BACKGROUND OF THE INVENTION

Regarding a skin cleansing agent such as a facial wash and a body soap, various studies have been conventionally made to obtain good foamability, a high cleansing effect, or moist feel after rinsing. In particular, the skin cleansing agent such as body soap is expected to have high foam volume and foam quality with fine texture during a cleansing process. For such reasons, developed is a skin cleansing agent having high lathering property during cleansing process by combining surfactants with high foamability or a cleansing agent having increased foam volume by combination with a commonly used cationic polymer and a non-ionic polymer for increasing liquid viscosity so that the created foam hardly disappear.

For example, Patent documents 1 and 2 disclose a cleansing composition containing an anionic surfactant and glyceryl ether having an alkyl group with from 4 to 12 carbon atoms. In addition, Patent document 3 discloses and studies a skin cleansing composition in which a detergent surfactant is combined with cationized cellulose.

Meanwhile, in recent days, with commonly occurring hair damages due to wide use of a coloring agent or a perming agent, it is important to provide a hair cleansing agent with an activity of providing a conditioning effect in addition to basic activities such as lathering and detergency.

Generally, in order to impart smoothness to the hair, combined use of an anionic surfactant and silicones (Patent Document 4) or combined use of an anionic surfactant and cationized cellulose is carried out.

CITATION LIST

Patent document

Patent Document 1: JP-A 2001-107097
Patent Document 2: JP-A 2001-115187
Patent Document 3: JP-A 2005-306843
Patent Document 4: JP-A 5-148123

SUMMARY OF THE INVENTION

The present invention is to provide a cleansing composition comprising the following components (A), (B), (C), and (D):

(A) an anionic surfactant,
(B) a glyceryl ether having an alkyl group or alkenyl group with from 4 to 12 carbon atoms,
(C) a cationized hydroxypropyl cellulose represented by the following formula (1), $$\left(\begin{array}{c} OR^1 \\ R^3O \underset{OR^2}{\overset{O}{\longleftrightarrow}} O \end{array}\right)_n \quad (1)$$

(in the formula, $R^1$, $R^2$ and $R^3$ each independently represent a substituent having a cationized ethyleneoxy group and a propyleneoxy group that are represented by the following formula (2) or (3), and n represents a number of from 20 to 5000, which represents the average polymerization degree of anhydroglucose, in which substitution degree of the cationized ethyleneoxy group is from 0.01 to 3 and substitution degree of the propyleneoxy group is from 0.01 to 5), $$R^1, R^2, R^3: \quad -\left(\begin{array}{cc} CH-CH-O \\ | \quad | \\ Y^1 \quad Y^2 \end{array}\right)_p (PO)_q - H \quad (2)$$

or $$R^1, R^2, R^3: \quad -(PO)_q \left(\begin{array}{cc} CH-CH-O \\ | \quad | \\ Y^1 \quad Y^2 \end{array}\right)_p - H \quad (3)$$

(in the formula, one of $Y^1$ and $Y^2$ represents a hydrogen atom and the other is a cationic group represented by the following formula (4), PO represents a propyleneoxy group, p represents the number of the cationized ethyleneoxy group ($-CH(Y^1)-CH(Y^2)-O-$) in the formula (2) or (3), q represents the number of the propyleneoxy group ($-PO-$) in the formula (2) or (3), each representing 0 or a positive number, in which, when none of p and q is 0, the cationized ethyleneoxy group and propyleneoxy group may be added in any order, and when at least one selected from p and q is 2 or higher, it may be any one of a block bond or a random bond)

$$Y^1, Y^2: \quad -\left[-CH_2 - \overset{R^4}{\underset{R^6}{\overset{|}{N^+}}} - R^5\right] X^- \quad (4)$$

(in the formula, $R^4$, $R^5$ and $R^6$ each independently represent a linear or branched alkyl group having from 1 to 3 carbon atoms, and $X^-$ represents an anionic group), and (D) water.

DETAILED DESCRIPTION OF THE INVENTION

A conventionally used skin cleansing composition has a problem that, although it has improved foamability, creamy foam is not provided. There is also a problem that, while having improved foamability, foams hardly disappear during rinsing process so that foams are easily remained in a drain. There is also a problem that, as slimy feel stays during rinsing process, it requires a large amount of water to have frictional feel like a fresh feeling expected from use of a soap.

In addition, according to the technique of cleansing hair described above, although smoothness is imparted to the hair, it is required to improve lathering, ease of movement of finger during bubbling, foam dissipation property, and residual feel during rinsing. For hair damaged by a chemical treatment or a heating treatment, in particular, when the movement of finger is not satisfactorily easy during bubbling, hands or fingers may be stuck between hairs during hair washing, thereby causing hair damage. In addition, although smoothness is given, there are cases in which foam dissipation property is poor so that residual feel remains during rinsing and slimy feel remains.

The present invention relates to a cleansing composition.

The present invention relates to a skin cleansing agent which has an excellent lathering property and high cleansing feel during use, can be easily washed off without slimy feel and has feel with frictional resistance (that is, stop feeling) during rinsing, and also has a property of hardly staying foams in a drain as the foam disappearance is quick.

The present invention relates to an aqueous hair cleansing agent which is excellent in lathering and foam quality so as to allow ease of movement of hand and finger during bubbling even in damaged hair, and has an excellent foam dissipation property during washing hair and suppressed residual feel during rinsing.

The present inventors found that, by combining a specific cationic polymer in addition to an anionic surfactant with specific glyceryl ether, a cleansing composition having not only an excellent foamability but also fast foam dissipation property can be obtained.

The cleansing composition of the present invention is characterized in that lathering is excellent during washing while foam dissipation property is fast during rinsing.

In case of a skin cleansing agent, it produces a large volume of foam during washing, foam quality is creamy and wash feel is excellent while it is easily washed off during rinsing, foam dissipation is fast, and foam hardly remains. In addition, it has suppressed residual feel during rinsing, it is possible to provide the skin immediately after towel drying after washing with the feel like the hands adsorbing onto the skin.

In case of a hair cleansing agent, it is excellent in lathering and foam quality, even in damaged hair, ease of movement of hand and finger during washing, and foam dissipation property is excellent during washing hair, and residual feel is suppressed during rinsing.

The anionic surfactant used as the component (A) in the invention is not specifically limited, and any of those commonly used for a cleansing composition can be used.

In case of a skin cleansing agent, examples thereof include alkyl sulfate, polyoxyalkylene alkyl ether sulfate, polyoxyalkylene alkenyl ether sulfate, sulfosuccinic acid alkyl ester salt, polyoxyalkylene sulfosuccinic acid alkyl ester salt, α-olefin sulfonate, fatty acid salt, alkyl ether carboxylate, N-acylamino acid salt, N-acylalkyl taurine salt, each having an alkyl group with from 10 to 22 carbon atoms or an acyl group with from 10 to 22 carbon atoms.

Among them, from the viewpoint of foamability or mildness on a skin, polyoxyalkylene alkyl ether sulfate, fatty acid salt, alkyl ether carboxylate, N-acylamino acid salt, and N-acylalkyl taurine salt are preferable, and alkyl ether carboxylate, N-acylamino acid salt, and N-acylalkyl taurine salt are more preferable.

Furthermore, from the viewpoint of formability, foam volume, and mildness on a skin, combination of alkyl ether carboxylate and polyoxyalkylene alkyl ether sulfate, combination of alkyl ether carboxylate and fatty acid salt, or combination of alkyl ether carboxylate and polyoxyalkylene alkyl ether sulfate and fatty acid salt are preferably used.

Further, examples of their salt include an alkali metal salt such as sodium and potassium; an alkali earth metal salt such as calcium and magnesium; an ammonium salt; alkanolamine salt such as monoethanol amine, diethanol amine, and triethanol amine; and basic amino acid salt such as arginine and lysine, and the like. Among them, from the viewpoint of less coloration of the composition, an alkali metal salt and an ammonium salt are preferable. An alkali metal salt is more preferable.

For an aqueous hair cleansing agent, specific examples thereof include sulfate type anionic surfactant such as alkyl sulfate, alkenyl sulfate, polyoxyalkylene alkyl ether sulfate, polyoxyalkylene alkenyl ether sulfate, and sulfosuccinic acid alkylene alkyl phenyl ether sulfate; sulfonic acid type anionic surfactant such as sulfosuccinic acid alkyl ester salt, polyoxyalkylene sulfosuccinic acid alkyl ester salt, and alkane sulfonate; and carboxylic acid type anionic surfactant such as higher fatty acid salt, alkyl ether carboxylic acid, or salt thereof. Among them, polyoxyalkylene alkyl ether sulfate, polyoxyalkylene alkenyl ether sulfate, alkyl sulfate, and alkenyl sulfate are preferable. As for the polyoxyethylene alkyl ether sulfate, those represented by the following formula (11) are preferable.

$$R^{11}O(CH_2CH_2O)_u SO_3 M \qquad (11)$$

(in the formula (11), $R^{11}$ represents an alkyl group or alkenyl group having from 10 to 18 carbon atoms, M represents an alkali metal, an alkali earth metal, ammonium, alkanolamine, or a basic amino acid, and u represents from 0.5 to 5 in weight average).

Among them, from the viewpoint of having both quick lathering and good feel of foams, it is preferable that $R^{11}$ in the above formula (11) is an alkyl group having from 12 to 14 carbon atoms. Further, an average mole number of the ethylene oxide added is preferably from 0.9 to 4, and more preferably from 1 to 3. In addition, polyoxyethylene alkyl ether sulfate in which M is ammonium or sodium is preferable.

One or two or more types of the component (A) may be used, and it is contained in the total composition of the cleansing agent in an amount of 3% by weight or more but 40% by weight or less, preferably 20% by weight or less.

In case of a skin cleansing agent, it is 3% by weight or more, preferably 5% by weight or more, more preferably 7% by weight or more, and is 40% by weight or less, preferably 20% by weight or less, and more preferably 15% by weight or less. Further, as a salt, it is contained in an amount of from 3 to 40% by weight, preferably from 5 to 20% by weight, and more preferably from 7 to 15% by weight in the total composition. When it is within this range, viscosity change of the cleansing composition due to change in temperature is small, and high cleansing property and formability as well as having less rough dry skin after washing can be obtained at the same time, and therefore desirable.

Further, in case of an aqueous hair cleansing agent, content of the component (A) is preferably 3% by weight or more, more preferably 5% by weight or more, and even more preferably 7% by weight or more in the total aqueous hair cleansing agent, from the viewpoint of further enhancing lathering. In addition, from the viewpoint of enhancing foam dissipation property and suppressing residual feel during rinsing, content of the component (A) is preferably 20% by weight or less, more preferably 18% by weight or less, and even more preferably 15% by weight or less.

Glyceryl ether as the component (B) used in the invention is obtained by an ether bonding between a linear or branched alkyl group or alkenyl group having from 4 to 12 carbon atoms and glycerin.

Specific examples of the alkyl group include a n-butyl group, an isobutyl group, a tert-butyl group, a n-pentyl group, a 2-methylbutyl group, an isopentyl group, a n-hexyl group, an isohexyl group, a n-heptyl group, a n-octyl group, a 2-ethylhexyl group, a n-nonyl group, a n-decyl group, an isodecyl group, and a n-lauryl group, and the like. Among them, those having from 4 to 11 carbon atoms are preferable. A linear or branched alkyl group having from 8 to 10 carbon atoms is more preferable. A 2-Ethylhexyl group and an isodecyl group are more preferable.

The component (B) is preferably monoalkyl glyceryl ether or monoalkenyl glyceryl ether. Those having one alkyl group with from 6 to 10 carbons, preferably one alkyl group with 8 carbon atoms are preferable. Isodecyl glyceryl ether and 2-ethylhexyl glyceryl ether are more preferable. 2-Ethylhexyl glyceryl ether is even more preferable in that it is hardly precipitated at low temperature and has high foamability.

One or two or more types of glyceryl ether may be used in the component (B), and it may be contained in an amount of 0.01% by weight or more and 10% by weight or less in the total cleansing composition.

In case of a skin cleansing agent, from the viewpoint of enhancing foamability of the cleansing agent and improving formability, it is 0.01% by weight or more, preferably 0.2% by weight or more, more preferably 0.4% by weight or more, and also 5% by weight or less, preferably 2% by weight or less, and more preferably 1.2% by weight or less in the total composition. Further, it is contained in an amount of from 0.01 to 5% by weight, preferably from 0.2 to 2% by weight, and more preferably from 0.4 to 1.2% by weight in the total composition.

Further, in case of an aqueous hair cleansing agent, it can be, for example, 0.01% by weight or more, preferably 0.05% by weight or more, and more preferably 0.1% by weight or more in the total aqueous hair cleansing agent, from the viewpoint of enhancing lathering. In addition, from the viewpoint of lowering frictional feel of hair during rinsing, content of the component (C) can be, for example, 5% by weight or less, preferably 4% by weight or less, and more preferably 3.5% by weight or less in the total aqueous hair cleansing agent.

The component (C) used in the invention is cationized hydroxypropyl cellulose represented by the formula (1), in which main chain derived from anhydroglucose is contained, substitution degree of the cationized ethyleneoxy group is from 0.01 to 3, and substitution degree of the propyleneoxy group is from 0.01 to 5 (herein after, also referred to as "C-HPC").

(Main Chain Derived from Anhydroglucose Represented by the Formula (1))

The main chain derived from anhydroglucose represented by the formula (1) has a main chain derived from anhydroglucose, as illustrated in the above formula (1).

In the formula (1), $R^1$, $R^2$ and $R^3$ each independently represent a substituent represented by the formula (2), and $R^1$, $R^2$ and $R^3$ may be the same or different from each other. In addition, each of $R^1$ in the number of n, $R^2$ in the number of n, and $R^3$ in the number of n may be the same or different from each other.

In case of a skin cleansing agent, from the viewpoint of imparting stop feeling property during rinsing after washing and good smoothness with moist feel of skin after drying, the average polymerization degree n in the formula (1) is 20 or higher, preferably 100 or higher, and more preferably 400 or higher. Further, it is 5000 or lower, preferably 2000 or lower, and more preferably 1300 or lower. Taken together the above points, the average polymerization degree n in the formula (1) is from 20 to 5000, preferably from 100 to 2000, and more preferably from 400 to 1300.

In case of an aqueous hair cleansing agent, the average polymerization degree n of anhydroglucose in the above formula (1) is, from the viewpoint of ease of movement of finger during lathering, 50 or higher, preferably 100 or higher, more preferably 200 or higher, and even more preferably 300 or higher. Further, from the viewpoint of suppressing residual feel during rinsing and improving the ease of production of the compound represented by the above formula (1), the average polymerization degree n is 5000 or lower, preferably 3000 or lower, more preferably 2000 or lower, and even more preferably 1500 or lower. Taken together the above points, the average polymerization degree n in the above formula (1) is from 50 to 5000, preferably from 100 to 3000, more preferably from 200 to 2000, and even more preferably, from 300 to 1500.

Meanwhile, as described herein, the average polymerization degree refers to a viscosity average polymerization degree that is measured by copper-ammonia method, and it is specifically calculated by the method described in Examples.

(Substituent Represented by the Formula (2) or (3))

In the formula (1), the substitution group represented by the formula (2) or (3) as $R^1$, $R^2$, or $R^3$ has, as illustrated in the above formula (2) or (3), a cationized ethyleneoxy group and a propyleneoxy group.

In the formula (2) or (3), one of $Y^1$ and $Y^2$ is a hydrogen atom, and the other is a cationic group represented by the formula (4), and PO represents a propyleneoxy group.

p represents the number of the cationized ethyleneoxy group (—CH($Y^1$)—CH($Y^2$)—O—) in the formula (2) or (3), and it is 0 or a positive number. From the viewpoint of ease of production, p is preferably 0 or 1.

q represents the number of the propyleneoxy group (—PO—) in the formula (2) or (3), and it is 0 or a positive number. From the viewpoint of ease of production, q is preferably a number of from 0 to 4, more preferably a number from 0 to 2, and even more preferably 0 or 1.

When a plurality of substituents represented by the formula (2) or (3) are present in a C-HPC molecule, each of p and q may be different in each substituents.

From the viewpoint of ease of production, sum of p and q is preferably a number of from 1 to 5, more preferably a number of from 1 to 4, even more preferably a number of from 1 to 3, and even more preferably 1 or 2.

When none of p and q is 0, the cationized ethyleneoxy group and propyleneoxy group may be added in any order. However, from the viewpoint of production efficiency, an order described in the formula (3) is more preferable.

In addition, when none of p and q is 0 and at least one selected from p and q is 2 or higher, it may be any one of block bond and random bond. From the viewpoint of ease of production, it is preferably a block bond.

With reference to at least one among $R^1$ in the number of n, $R^2$ in the number of n and $R^3$ in the number of n, p in the formula (2) or (3) is not 0, and also with reference to at least one among them, q in the formula (2) or (3) is not 0.

(Cationic Group Represented by the Formula (4))

In the formula (2) or (3), the cationic group represented by the formula (4) as $Y^1$ and $Y^2$ has a structure represented by the above formula (4).

$R^4$, $R^5$ and $R^6$ in the formula (4) independently represent a linear or branched alkyl group having from 1 to 3 carbon atoms, and specific examples thereof include a methyl group, an ethyl group, a n-propyl group and an isopropyl group. Among them, from the viewpoint of water solubility of C-HPC, a methyl group and an ethyl group are preferable, and a methyl group is more preferable.

In the formula (4), $X^-$ represents an anionic group as a counter ion of the ammonium group. $X^-$ is not limited, as long as it is an anionic group. Specific examples thereof include an alkyl sulfate ion, a sulfate ion, a phosphate ion, an alkyl carbonate ion, and a halide ion, and the like. Among them, from the viewpoint of ease of production, a halide ion is preferable. Examples of the halide ion include a fluoride ion, a chloride ion, a bromide ion, and an iodide ion. From the viewpoint of water solubility and chemical stability of C-HPC, a chloride ion and a bromide ion are preferable, and a chloride ion is more preferable.

In C-HPC represented by the formula (1), substitution degree of the cationized ethyleneoxy group is from 0.01 to 3.

When the cleansing composition of the present invention is a skin cleansing agent, from the viewpoint of having feel with frictional resistance during rinsing after washing (stop feeling), and imparting good feel with moist feel to the skin after drying, the substitution degree of the cationized ethyleneoxy group is preferably from 0.01 to 3, more preferably from 0.1 to 2.4, and even more preferably from 0.18 to 1.

When the cleansing composition of the present invention is an aqueous hair cleansing agent, from the viewpoint of acquiring a favorable lathering, ease of movement of finger and foam dissipation property during bubbling even for damaged hair, during washing hair, suppressing residual feel during rinsing, and ease of production, the substitution degree of the cationized ethyleneoxy group is 2.9 or lower, preferably 2.0 or lower, more preferably 1.0 or lower, and even more preferably 0.5 or lower. In addition, from the viewpoint of having favorable lathering during washing hair with an aqueous hair cleansing agent, favorable foam dissipation property, ease of movement of finger during washing, and suppressing residual feel during rinsing, the substitution degree of the cationized ethyleneoxy group is 0.01 or higher and preferably 0.02 or higher. Taken together the above points, it is from 0.01 to 2.9, preferably from 0.01 to 2.0, more preferably from 0.02 to 1.0, and even more preferably from 0.02 to 0.5.

According to the invention, the substitution degree of the cationized ethyleneoxy group means the average mole number of the cationized ethyleneoxy group that is present in a C-HPC molecule per mole of anhydroglucose unit constituting the cellulose main chain. The substitution degree of the cationized ethyleneoxy group is measured in accordance with the method described in the following Examples.

Further, the substitution degree of the propyleneoxy group is from 0.01 to 5.

When the cleansing composition of the present invention is a skin cleansing agent, from the viewpoint of imparting a high level of formability during washing and foam dissipation property during rinsing, and de-foamability, the substitution degree of the propyleneoxy group is from 0.01 to 5, preferably from 0.2 to 3, and more preferably from 1.1 to 2.9.

When the cleansing composition of the present invention is an aqueous hair cleansing agent, the substitution degree of the propyleneoxy group is preferably from 0.1 to 4, and from the viewpoint of acquiring favorable lathering, ease of movement of finger and dissipation property during bubbling even for damaged hair, during washing hair, suppressing residual feel during rinsing, and ease of production, the substitution degree of the propyleneoxy group is 4.0 or lower, preferably 3.0 or lower, more preferably 2.5 or lower, and even more preferably 2.1 or lower. In addition, from the viewpoint of acquiring favorable lathering, favorable dissipation property and ease of movement of finger during bubbling even for damaged hair, during washing hair with an aqueous hair cleansing agent and suppressing residual feel during rinsing, the substitution degree of the propyleneoxy group is 0.1 or higher, preferably 0.2 or higher, more preferably 0.5 or higher, and even more preferably 0.8 or higher. Taken together the above points, the substitution degree of the propyleneoxy group is from 0.1 to 4.0, preferably from 0.2 to 3.0, more preferably from 0.5 to 2.5, and even more preferably from 0.8 to 2.1.

According to the invention, the substitution degree of the propyleneoxy group means the average mole number of the propyleneoxy group that is present in a C-HPC molecule per mole of anhydroglucose unit constituting the cellulose main chain. The substitution degree of the propyleneoxy group is measured in accordance with the method described in the following Examples.

Further, when the cleansing composition of the present invention is an aqueous hair cleansing agent, sum of the substitution degree of the cationized ethyleneoxy group and the substitution degree of the propyleneoxy group is preferably 3.2 or lower, more preferably 3.0 or lower, and even more preferably 2.5 or lower. In addition, from the viewpoint of acquiring light foam quality to have ease of movement of hands and fingers even in damaged hair during hair washing with an aqueous hair cleansing agent, suppressing slimy feel during hair washing, and excellent foam dissipation property after hair washing, it is 0.11 or higher, preferably 0.2 or higher, and more preferably 0.3 or higher. Taken together the above points, sum of the substitution degree of the cationized ethyleneoxy group and the substitution degree of the propyleneoxy group is preferably from 0.11 to 3.2, more preferably from 0.2 to 3.0, and even more preferably from 0.3 to 2.5.

Further, as for the combination of $R^1$, $R^2$ and $R^3$ in the above formula (1), for example, a constitution as follows can be mentioned;

with regard to $R^1$, p=1 and q=0 in the above formula (2), one of $Y^1$ and $Y^2$ is a hydrogen atom and the other is a cationic group represented by the above formula (4), all of $R^4$, $R^5$ and $R^6$ in the above formula (4) are a methyl group, and $X^-$ is a chloride ion; and with regard to $R^2$ and $R^3$, p=0 and q=0 or 1 in the above formula (2).

C-HPC of the component (C) can be obtained by the following production methods (1) to (3), for example.

(1) Cellulose, water in a large amount, and alkali metal hydroxide in an excess amount are mixed in slurry state, and reacted with a cationizing agent and propylene oxide.

(2) By using dimethyl acetamide containing lithium chloride as a solvent and further dissolving cellulose by adding amines or an alcoholate catalyst, and reacted with a cationizing agent and propylene oxide.

(3) Without using water in an excess amount or solvent as is the case of the above (1) and (2), cellulose in powder, pellet, or chip form, a cationizing agent, and propylene oxide are reacted with one another in the presence of a base.

According to the above production methods (1) to (3), the reaction with a cationizing agent and the reaction with propylene oxide may be carried out in any order or may be carried out simultaneously.

Among the above production methods, from the viewpoint of ease of production, the production method (3) is preferable.

C-HPC as the component (C) is preferably contained in an amount of 0.01% by weight or more and 10% by weight or less in the total composition.

In case of a skin cleansing agent, from the viewpoint of imparting foam volume and foam quality during washing, ease of disappearance of foam during rinsing, stop feeling property during rinsing after washing and imparting good feel with moist feel to skin after drying, it is 0.01% by weight or more, preferably 0.2% by weight or more, and more preferably 0.5% by weight or more in the total composition. In addition, it is 10% by weight or less, preferably 2% by weight or less, and more preferably 1.4% by weight or less in the total composition. Taken together the above points, it is contained in an amount of from 0.01 to 10% by weight, preferably from 0.2 to 2% by weight, and more preferably from 0.5 to 1.4% by weight in the total composition.

In case of an aqueous hair cleansing agent, from the viewpoint of acquiring high lathering property by increasing foam stability while ensuring ease of movement of finger during bubbling, in the total aqueous hair cleansing agent, the lower limit is preferably 0.01% by weight or more, more preferably 0.02% by weight or more, even more preferably 0.05% by weight or more, and even more preferably 0.1% by weight or more. Further, from the viewpoint of improving foam dissipation property and suppressing residual feel during rinsing, in the total aqueous hair cleansing agent, the upper limit is preferably 10% by weight or less, more preferably 5% by weight or less, even more preferably 2% by weight or less, and even more preferably 1% by weight or less. Taken together the above points, content of C-HPC is preferably from 0.01 to 10% by weight, more preferably from 0.02 to 5% by weight, even more preferably from 0.05 to 2% by weight, and even more preferably from 0.1 to 1% by weight in the total composition.

According to the invention, by combining the components (A), (B) and (C), foamability and foam volume are improved during washing, and thus good wash feel can be imparted. Meanwhile, with the above composition, foamability is significantly lowered when highly diluted with water, thus foams are dripping from the skin and are easily defoamed when flushed with shower water and the like so that they do not stay in a drain in a bathroom, a wash bowl and the like. Therefore, an amount of water used for rinsing can be significantly reduced.

In case of an aqueous hair cleansing agent, weight ratio of the component (C) to the component (A) (the component (C)/the component (A)) can be 0.0005 or higher, for example, from the viewpoint of acquiring high lathering property by increasing foam stability while obtaining ease of movement of finger during bubbling. It is preferably 0.001 or higher, and more preferably 0.006 or higher. Further, from the viewpoint of improving foam dissipation property and suppressing residual feel during rinsing, in the aqueous hair cleansing agent of the present invention, the component (C)/the component (A) can be 0.5 or less, for example. Preferably, it is 0.1 or less, and more preferably 0.05 or less.

When the cleansing composition of the present invention is a skin cleansing agent, if weight ratio of the component (C) to the component (B) ((C)/(B)) is from 0.2 to 6, moist feel like the hands adsorbing onto the skin is obtained immediately after towel drying after washing. Further, if (C)/(B) is from 0.4 to 3.5, it can provide the skin after drying with the smoothness with moist feel, and therefore desirable.

When the cleansing composition of the present invention is an aqueous hair cleansing agent, a weight ratio of the component (C) to the component (B) (the component (C)/the component (B)) can be 0.002 or higher from the viewpoint of enhancing foam stability. It is preferably 0.004 or higher, and more preferably 0.01 or higher. Further, from the viewpoint of a balance between favorable lathering and foam dissipation property and suppression of residual feel during rinsing, in the aqueous hair cleansing agent of the present invention, the component (C)/the component (B) can be 50 or less, for example. Preferably, it is 5 or less, and more preferably 2 or less.

Water as the component (D) may be present as a remaining amount of each component, and may be contained in an amount of 35% by weight or more, preferably 40% by weight or more and 95% by weight or less in the total composition.

In case of a skin cleansing agent, it is preferably 35% by weight or more and 95% by weight or less, and more preferably 50% by weight or more and 80% by weight or less in the total composition.

In case of an aqueous hair cleansing agent, it is preferably 50% by weight or more and 95% by weight or less, and more preferably 60% by weight or more and 90% by weight or less in the total composition.

When the cleansing composition of the present invention is a skin cleansing agent, it may contain, as the component (E), a polymer other than the component (C). Examples of the polymer as the component (E) include (E1) cationic polymer, (E2) anionic polymer, (E3) non-ionic polymer, and (E4) amphoteric polymer.

By using the component (E) in combination with the components (A), (B) and (C), foam quality during washing can be improved.

As for the (E1) cationic polymer, those with cation charge density of less than 4.5 are preferable and examples thereof include, as a copolymer of diallyl dialkyl quaternary ammonium salt (DMDAAC)/acrylamide (AM), MERQUAT 550 (weight average molecular weight: 160,000, cation charge density: 4.22 meq/g, DMDAAC:AM=50:50), MERQUAT 2200 (weight average molecular weight: 90,000, cation charge density: 4.22 meq/g, DMDAAC:AM=50:50), MERQUAT S (weight average molecular weight: 260,000, cation charge density: 4.22 meq/g, DMDAAC:AM=50:50) [copolymer of acrylamide and diallyl dimethyl ammonium salt, all manufactured by NALCO]; POISE C-60H (weight average molecular weight: 600,000, cation charge density: from 1.07 to 1.78 meq/g), CATICELO M-80 (weight average molecular weight: 800,000, cation charge density: from 0.93 to 1.21 meq/g), POISE C-150L (weight average molecular weight: 1,500,000, cation charge density: from 0.71 to 1.07 meq/g) [cationized cellulose (O-[2-hydroxy-3-(trimethylammonio) propyl]hydroxyethyl cellulose chloride), all manufactured by Kao Corporation]; JAGUAR C17 (weight average molecular weight: 300,000, cation charge density: from 1.07 to 1.50 meq/g), JAGUAR C14 (weight average molecular weight: 300,000, cation charge density: from 0.93 to 1.21 meq/g) [cationized guar gum (guar hydroxypropyl triammonium chloride), all manufactured by Rhodia]; and LUVIQUAT FC550 (weight average molecular weight: 80,000, cation charge density: 3.3 meq/g), LUVIQUAT FC370 (weight average molecular weight: 100,000, cation charge density: 2 meq/g) [3-methyl-1-vinyl-1H-imidazolium chloride.1-vinyl-2-pyrrolidone copolymer, all manufactured by BASF SE].

Examples of the (E2) anionic polymer include, having a sugar skeleton, sodium stearoxy PG hydroxyethyl cellulose sulfonate (INCI: SODIUM STEAROXY PG-HYDROXYETHYL CELLULOSE SULFONATE) (POISE 310 (Kao Corporation)), and also commercially available products such as xanthan gum, carrageenan and locust bean gum. Further, examples of a polymer of acrylic acid and/or methacrylic acid include alkyl acrylate.alkyl methacrylate.polyoxyethylene (20) stearyl ether copolymer (INCI: ACRYLATES/STEARETH-20 METHACRYLATE COPOLYMER), alkyl acrylate.alkyl methacrylate.polyoxyethylene (25) lauryl ether copolymer (INCI: ACRYLATES/LAURETH-25 METHACRYLATE COPOLYMER), alkyl acrylate.alkyl methacrylate.polyoxyethylene (25) behenyl ether copolymer (INCI: ACRYLATES/BEHENETH-25 METHACRYLATE COPOLYMER), acrylic acid.alkyl methacrylate copolymer (INCI: ACRYLATES/C10-30 ALKYL ACRYLATE CROSSPOLYMER), acrylic acid.neodecanoic acid vinyl copolymer (INCI: ACRYLATES/VINYL NEODECANOATE CROSSPOLYMER), (alkyl acrylate.octylacrylamide) copolymer (INCI: ACRYLATES/OCTYLACRYLAMIDE COPOLYMER), (acrylate/steareth-20 itaconate) copolymer (INCI: ACRYLATES/STEARETH-20 ITACONATE COPOLYMER), (acrylate/ceteth-20 itaconate) copolymer (INCI: ACRYLATES/CETETH-20 ITACONATE COPOLYMER), and (acrylate/aminoacrylate/C10-30 alkyl PEG-20 itaconic acid) copolymer (INCI: ACRYLATES/

AMINOACRYLATES/C10-30ALKYL PEG-20 ITACONATE COPOLYMER), and the like.

Further examples of such polymers include commercial products, such as ACULYN 88, ACULYN 22, ACULYN 28 and ACULYN 38 (each manufactured by Rohm and Haas Japan Company), CARBOPOL ETD 2020, CARBOPOL Ultrez 21, CARBOPOL Ultrez 20, PEMULEN TR-1 and PEMULEN TR-2 (each manufactured by Lubrizol Advanced Materials), and STRUCTURE 2001, STRUCTURE 3001, STRUCTURE PLUS and DERMACRYL 79 (each manufactured by Japan NSC).

Examples of the (E3) non-ionic polymer include hydroxyethyl cellulose, hydroxypropylmethyl cellulose, hydroxypropyl guar gum, polyvinyl pyrrolidone, polyethylene glycol, and the like. Among them, hydroxypropyl guar gum and polyethylene glycol are more preferable. Weight average molecular weight of them is preferably from 40,000 to 3,000,000, and more preferably from 300,000 to 2,750,000, and even more preferably from 2,000,000 to 2,500,000.

As the non-ionic polymer, commercially available products as follows can be used; ALKOX series (Meisei Chemical Works, Ltd., polyethylene glycol): ALKOX E30 (weight average molecular weight of from 300,000 to 500,000), ALKOXE-45 (weight average molecular weight of from 600,000 to 800,000) ALKOXE-60 (weight average molecular weight of from 1,000,000 to 1,200,000), ALKOX E-75 (weight average molecular weight of from 2,000,000 to 2,500,000), ALKOX E-100 (weight average molecular weight of from 2,500,000 to 3,000,000); METOLOSE series (Shin-Etsu Chemical Co., Ltd., hydroxypropylmethyl cellulose): METOLOSE 60SH-10000 (weight average molecular weight of 380,000); JAGUAR HP series (hydroxypropyl guar gum manufactured by Rhodia), JAGUAR HP8, HP105, HP-120 (all with weight average molecular weight of 2,200,000), and the like.

Examples of the (E4) amphoteric polymer include a copolymer of dimethyl diallyl ammonium chloride, acrylic acid and acrylamide (product name: MERQUAT Plus 3330, MERQUAT Plus 3331; manufactured by Ondeo Nalco Company), MERQUAT S (weight average molecular weight: 260,000, cation charge density: 4.22 meq/g, DMDAAC:AM=50:50), and the like.

One or two or more types of the component (E) can be used. When the component (E) is contained, from the viewpoint of improving foam quality without lowering foam volume, it is contained preferably in an amount of 0.01% by weight or more, more preferably 0.1% by weight or more, and even more preferably 0.3% by weight or more in the total composition. Further, it is preferably contained in an amount of 4% by weight or less, more preferably 2.1% by weight or less and even more preferably 1.4% by weight or less in the total composition. Taken together the above points, it is contained preferably in an amount of from 0.01 to 4% by weight, more preferably from 0.1 to 2.1% by weight, and even more preferably from 0.3 to 1.4% by weight in the total composition.

Among the component (E), the components (E1) and (E2) are preferable from the viewpoint of enhancing stop feeling effect during rinsing.

In addition, when the components (E1) and (E2) are contained, (E1)/(C)=from 0.1 to 5, and more preferably from 0.2 to 2 in terms of the weight ratio between the component (C) and the component (E). Further, when (E2)/(C)=from 0.1 to 5, and preferably from 0.2 to 2, stop feeling effect can be given at high level with improved foam quality, and therefore desirable.

When the cleansing composition of the present invention is a skin cleansing agent, alkyl polyglycoside-based non-ionic surfactant and/or polyoxyethylene alkyl ether-based non-ionic surfactant may be contained as the component (F). By using them, high foam volume can be obtained during washing and moist feel like the hands adsorbing onto the skin can be given after tower drying following cleansing.

Alkyl polyglycosides are a non-ionic surfactant derived from sugars and higher alcohols, and examples include those represented by the following formula.

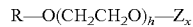

(in the formula, R represents an alkyl group having from 9 to 20 carbon atoms, h represents, on average, a number of 0 or higher and 10 or lower, Z represents a sugar residue having 5 or 6 carbon atoms, and x represents, on average, a number of from 1 to 5).

In the formula, R is preferably an alkyl group having from 6 to 16 carbon atoms, and it may be a mixture of them. Z is preferably pentose or hexose, and among them, glucose is more preferable. h is, on average, preferably a number of from 0 to 5, and x is, on average, a number of from 1 to 3.

As the polyoxyethylene alkyl ether-based non-ionic surfactant, those having an alkyl group with from 12 to 22 carbon atoms, and those having from 10 to 30 moles of polyoxyethylene group added thereto are preferable. Specific examples thereof include polyoxyethylene lauryl ether, polyoxyethylene myristyl ether, polyoxyethylene palmityl ether, polyoxyethylene isostearyl ether, polyoxyethylene stearyl ether, polyoxyethylene oleyl ether, polyoxyethylene hexyldecyl ether, polyoxyethylene octyldodecyl ether, and polyoxyethylene behenyl ether, and the like.

Further, polyoxyethylene alkyl ether-based non-ionic surfactants having HLB of from 10 to 20, and also having HLB of from 13 to 16 are more preferable because a cleansing composition having more excellent transparency can be obtained.

It should be noted that HLB is an index indicating a balance between hydrophilicity and lipophilicity (Hydropile Balance), and in the invention, the values calculated in accordance with the equation by Oda and Teramura et al are used.

$$HLB = \frac{\Sigma \text{ Inorganic value}}{\Sigma \text{ Organic value}} \times 10$$

Examples of the polyoxyethylene alkyl ether-based non-ionic surfactant that is preferably used include polyoxyethylene (21) lauryl ether (EMULGEN 121-G (HLB 14), manufactured by Kao Corporation), polyoxyethylene (20) 2-hexyldecyl ether (EMULGEN 1620 G (HLB 14), manufactured by Kao Corporation), polyoxyethylene (20) octyl dodecyl ether (EMULGEN 2020 G (HLB 13), manufactured by Kao Corporation), and polyoxyethylene (16) lauryl ether (EMULGEN 116 (HLB 15.8), manufactured by Kao Corporation), and the like.

As for the component (F), from the viewpoint of having excellent skin feel after towel drying after cleansing, alkyl polyglycoside is preferable.

One or more types of the component (F) can be used. When it is contained, from the viewpoint of foam volume of the cleansing composition and touch feel during rinsing, it is preferably contained in an amount of 0.05% by weight or more, more preferably 0.2% by weight or more, and even more preferably 0.5% by weight or more in the total composition. Further, it is preferably contained in an amount of 10% by weight or less, more preferably 6% by weight or less, and even more preferably 4% by weight or less in the total composition. Taken together the above points, it is preferably contained in an amount of from 0.05 to 10% by weight, more preferably from 0.2 to 6% by weight, and even more preferably from 0.5 to 4% by weight in the total composition.

When the cleansing composition of the present invention is a skin cleansing agent, (G) amphoteric surfactant may be contained.

Examples of the amphoteric surfactant include carbobetaine, sulfobetaine, imidazolinium betaine, and amide betaine, and the like, and by using it, lathering can be further improved without impairing rinse feel. Specific examples thereof include fatty acid amide propylbetaine and hydroxy propyl sulfobetaine, and the like.

One or two or more types of the component (G) can be used. When it is contained, it is preferably contained in an amount of from 0.1 to 10% by weight, and also from 0.5 to 6% by weight in the total composition, from the viewpoint of improving foamability.

When the cleansing composition of the present invention is a skin cleansing agent, polyol may be also contained, and as a result, the low temperature stability and moisture retaining property by skin can be improved.

The polyol is a polyhydric alcohol having two or more hydroxy groups in the molecule, and specific examples thereof include alkylene glycol such as ethylene glycol, propylene glycol, 1,3-butylene glycol, and 1,4-butylene glycol; polyalkylene glycol such as dipropylene glycol; sugar alcohols such as glucose, maltose, maltitose, sucrose, fructose, xylitol, sorbitol, maltotriose, and threitol; and glycerin, polyglycerin, erythritol, and alcohol obtained by degradation and reduction of starch, and the like.

One or more type of polyol may be used. When it is contained, it is preferably contained in an amount of from 0.1 to 40% by weight, more preferably from 1 to 20% by weight, and even more preferably from 3 to 10% by weight in the total composition.

When the cleansing composition of the present invention is a skin cleansing agent, it may further comprise other components used in ordinary cleansing composition such as an oily component, an anti-bacterial agent, an anti-inflammatory agent, a preservative, a chelating agent, salts, a pearlescent agent, a scrubbing agent, a fragrance, a cooling agent, a pigment, an UV absorbing agent, an antioxidant, plant extract, and the like.

When the cleansing composition of the present invention is an aqueous hair cleansing agent, it may comprise components other than the components (A) to (D).

In case of an aqueous hair cleansing agent, constitution containing a cationized polymer other than the component (B) can be adopted. Examples of the cationized polymer other than the component (B) comprise cationized cellulose derivatives such as cationized hydroxyethyl cellulose; cationized starch; cationized galactomannan and derivatives thereof such as cationized fenugreek gum, cationized guar gum, cationized tara gum, cationized locust bean gum; and copolymers such as diallyl quaternary ammonium salt/acrylamide copolymer, vinylimidazolium trichloride/vinyl pyrrolidone copolymer, hydroxyethyl cellulose/dimethyl diallyl ammonium chloride copolymer, vinyl pyrrolidone/quaternized dimethylaminoethyl methacrylate copolymer, polyvinyl pyrrolidone/alkylaminoacrylate copolymer, polyvinyl pyrrolidone/alkylaminoacrylate/vinyl caprolactam copolymer, vinyl pyrrolidone/methacrylamide propyl trimethyl ammonium chloride copolymer, alkylacrylamide/acrylate/alkylaminoalkylacrylamide/polyethylene glycol methacrylate copolymer, and adipic acid/dimethylaminohydroxypropylethylene triamine copolymer (CARTARETINE, manufactured by Sandoz, USA), the cationic polymer described in JP-A No. 53-139734, the cationic polymer described in JP-A 60-36407, and the like.

Among them, from the viewpoint of lowering stickiness or frictional feel of hair during rinsing, one or more types selected from the group consisting of cationized guar gum, cationized tara gum and cationized hydroxyethyl cellulose is preferably used.

Among them, the cationized galactomannan is a water soluble cationized polymer obtained by introducing a quaternary nitrogen-containing group to galactomannan having a main chain consisting of mannose unit and a side chain consisting of galactose unit. Galactomannan is obtained from the endosperm of leguminous seeds, for example. When the ratio of galactose and mannose is 1:1, it corresponds to fenugreek gum. When it is 1:2, it corresponds to guar gum. When it is 1:3, it corresponds to tara gum. When it is 1:4, it corresponds to locust bean gum.

Examples of the commercially available product of cationized galactomannan include cationized fenugreek gum as CATINAL CF-100 (manufactured by TOHO Chemical Industry Co., Ltd.). Examples of the commercially available product of cationized guar gum include JAGUAR series such as JAGUAR C-13S, JAGUAR C-14S, and JAGUAR C-17 (manufactured by Rhodia, guar hydroxypropyl triammonium chloride) and the like. In addition, examples of the commercially available product of cationized tara gum include CATINAL CTR-100, CATINAL CTR-200 (all manufactured by TOHO Chemical Industry Co., Ltd.) and the like. Further, examples of the commercially available product of cationized locust bean gum include CATINAL CLB-100 (manufactured by TOHO Chemical Industry Co., Ltd., locust bean hydroxypropyl triammonium chloride) and the like.

Further, examples of other commercially available product which may be used as the cationized polymer other than the component (B) include MERQUAT 550 (manufactured by NALCO, copolymer of acrylamide and diallyl dimethyl ammonium salt; INCI name POLYQUATERNIUM-7), LUVIQUAT FC370 (manufactured by BASF, copolymer of 1-vinyl-2-pyrrolidone and 1-vinyl-3-methyl imidazolium salt; INCI name POLYQUATERNIUM-16), GAFQUAT 755N (manufactured by ISP, copolymer of 1-vinyl-2-pyrrolidone and dimethylaminoethyl methacrylate; INCI name POLYQUATERNIUM-11), UCARE polymer JR and the same UCARE LR series (manufactured by Amcol, a salt of reaction product of trimethyl ammonium substituted epoxide and hydroxyethyl cellulose; and INCI name POLYQUATERNIUM-10), POISE C-60H, POISE C-80M, POISE C-150L (all manufactured by Kao Corporation, a salt of reaction product of trimethyl ammonium-substituted epoxide and hydroxyethyl cellulose; INCI name POLYQUATERNIUM-10), and the like.

Two or more types of the cationized polymer other than the component (B) may be used in combination. From the viewpoint of lowering frictional feel of hair during rinsing, the content may be, to the total aqueous hair cleansing agent of the present invention, from 0.01 to 3% by weight, and is preferably from 0.02 to 2% by weight, and more preferably from 0.05 to 1% by weight.

When the cleansing composition of the present invention is an aqueous hair cleansing agent, to further improve the cleansing performance, it may also comprise a non-ionic surfactant or an amphoteric surfactant.

Examples of the non-ionic surfactant include polyoxyalkylene sorbitan fatty acid esters, polyoxyalkylene sorbit fatty acid esters, polyoxyalkylene glycerin fatty acid esters, polyoxyalkylene fatty acid esters, polyoxyalkylene alkyl ethers, polyoxyalkylene alkyl phenyl ethers, polyoxyalkylene (hydrogenated) castor oils, sucrose fatty acid esters, polyglycerin alkyl ethers, polyglycerin fatty acid esters, fatty acid alkanolamide, alkyl glycosides, and monoalkenyl glyceryl ethers, and the like.

Among them, polyoxyalkylene sorbitan fatty acid esters such as polyoxyethylene sorbitan fatty acid ester, polyoxyalkylene fatty acid esters such as polyoxyalkylene (C8 to C20) fatty acid ester, polyoxyalkylene (hydrogenated) castor oils such as polyoxyethylene hydrogenated castor oils, and alkyl glycosides are preferable.

Fatty acid alkaonolamide is also preferable, and any one of monoalkanol amide and dialkanol amide can be used. Those having an acyl group with from 8 to 18 carbon atoms, in particular from 10 to 16 carbon atoms are preferable. Further, those having a hydroxyalkyl group with from 2 to 3 carbon atoms are preferable. Examples thereof include oleic acid diethanol amide, palm kernel oil fatty acid diethanol amide, coconut oil fatty acid diethanol amide, lauric acid diethanol amide, polyoxyethylene coconut fatty acid monoethanol amide, coconut fatty acid monoethanol amide, lauric acid isopropanol amide, and lauric acid monoethanol amide, and the like.

Examples of the amphoteric surfactant include a betaine-based surfactant. Among them, alkyl dimethylaminoacetic acid betaine, fatty acid amide propylbetaine, alkylhydroxysulfobetaine, and the like are preferable. Fatty acid amide propylbetaine is particularly preferable. As for the fatty acid amide propylbetaine, those having an acyl group with from 8 to 18 carbon atoms, in particular from 10 to 16 carbon atoms are preferable. In particular, lauric acid amide propylbetaine, palm kernel oil fatty acid amide propylbetaine, and coconut fatty acid amide propylbetaine, and the like are preferable.

Other examples of the amphoteric surfactant include a sultaine-based surfactant such as laurylhydroxy sultaine.

The non-ionic surfactant or amphoteric surfactant may be used either singly or in combination of two or more in the aqueous hair cleansing agent. When the aqueous hair cleansing agent of the present invention is prepared as an aqueous liquid type cleansing agent, if fatty acid amide propylbetaine, fatty acid alkanolamide or monoalkyl glyceryl ether is used in combination with the component (A), not only the formability is improved but also a suitable liquid property is obtained, and therefore particularly preferable.

Further, content of the non-ionic surfactant or amphoteric surfactant can be, for example, from the viewpoint of obtaining favorable lathering effect, from 0.01 to 15% by weight, and is preferably from 0.05 to 8% by weight, and more preferably from 0.1 to 6% by weight in the total aqueous hair cleansing agent of the present invention.

When the cleansing composition of the present invention is an aqueous hair cleansing agent, a cationic surfactant or silicones may be further added to improve the finish feel after drying.

Examples of the cationic surfactant include (i) alkyltrimethyl ammonium salt, (ii) alkoxytrimethyl ammonium salt, (iii) dialkyldimethyl ammonium salt, (iv) alkyldimethylamine and a salt thereof, (v) alkoxydimethylamine and a salt thereof, (vi) alkylamide dimethylamine and a salt thereof, and the like.

(i) Alkyltrimethyl Ammonium Salt:

Examples of the alkyltrimethyl ammonium salt include those represented by the following formula.

$$R^{22}-N^+(CH_3)_3Z^-$$

(in the formula, $R^{22}$ represents an alkyl group having from 12 to 22 carbon atoms and $Z^-$ represents a halide ion such as chloride ion and bromide ion).

More specific examples thereof include cetyl trimethyl ammonium chloride, stearyl trimethyl ammonium chloride, and behenyl trimethyl ammonium chloride, and the like.

(ii) Alkoxytrimethyl Ammonium Salt:

Examples of the alkoxytrimethyl ammonium salt include those represented by the following formula.

$$R^{23}-O-R^{24}-N+(CH_3)_3Z^-$$

(in the formula, $R^{23}$ represents an alkyl group having from 12 to 22 carbon atoms, $R^{24}$ represents an ethylene group or a propylene group which may be substituted with a hydroxy group, and $Z^-$ is as defined above).

More specific examples thereof include stearoxypropyltrimethyl ammonium chloride, stearoxyethyltrimethyl ammonium chloride, and stearoxyhydroxypropyltrimethyl ammonium chloride, and the like.

(iii) Dialkyldimethyl Ammonium Salt:

Examples of the dialkyldimethyl ammonium salt include those represented by the following formula.

$$(R^{25})_2N^+(CH_3)_2Z^-$$

(in the formula, $R^{25}$ independently represents an alkyl group or benzyl group having from 12 to 22 carbon atoms and $Z^-$ is as defined above).

More specific examples thereof include distearyldimethyl ammonium chloride, and the like.

(iv) Alkyl Dimethylamine and a Salt Thereof:

Examples of the alkyl dimethylamine and a salt thereof include those represented by the following formula.

$$R^{26}-N(CH_3)_2$$

(in the formula, $R^{26}$ represents an alkyl group having from 12 to 22 carbon atoms).

More specific examples thereof include behenyldimethylamine and stearyldimethylamine, and an organic acid salt thereof.

(v) Alkoxydimethylamine and a Salt Thereof:

Examples of the alkoxydimethylamine and a salt thereof include those represented by the following formula.

$$R^{27}-O-R^{28}-N(CH_3)_2$$

(in the formula, $R^{27}$ represents an alkyl group having from 12 to 22 carbon atoms and $R^{28}$ represents an ethylene group or a propylene group).

(vi) Alkylamide Dimethylamine and a Salt Thereof:

Examples of the alkylamide dimethylamine and a salt thereof include those represented by the following formula, and a salt thereof.

$$R^{29}-C(=O)NH-R^{30}-N(CH_3)_2$$

(in the formula, $R^{29}$ represents an alkyl group having from 11 to 21 carbon atoms and $R^{30}$ represents an ethylene group or a propylene group).

Examples of the cationic surfactant other than the above (i) to (vi) include ethyl sulfuric acid lanolin fatty acid aminopropylethyl dimethyl ammonium (ethyl sulfate salt of alkanoylaminopropyl dimethylethyl ammonium, in which the alkanoyl group is derived from lanolin), ethyl sulfuric acid lanolin fatty acid aminoethyl triethyl ammonium, ethyl sulfuric acid lanolin fatty acid aminopropyl triethyl ammonium, methyl sulfuric acid lanolin fatty acid aminoethyl trimethyl ammonium, methyl sulfuric acid lanolin fatty acid aminopropylethyl dimethyl ammonium, ethyl sulfuric acid isoalkanoic acid (C14 to C20) aminopropylethyl dimethyl ammonium, ethyl sulfuric acid isoalkanoic acid (C18 to C22) aminopropylethyl dimethyl ammonium, ethyl sulfuric acid isostearic acid aminopropylethyl dimethyl ammonium, ethyl sulfuric acid isononanoic acid aminopropylethyl dimethyl ammonium and alkyltrimethyl ammonium saccharine, and the like.

The cationic surfactant may be used in combination of two or more types. From the viewpoint of smoothness from washing to rinsing, the content is preferably from 0.01 to 10% by weight, more preferably from 0.02 to 6% by weight, and even more preferably from 0.05 to 3% by weight in the aqueous hair cleansing agent of the present invention.

Examples of the silicones include the following.
(I) Dimethylpolysiloxane:

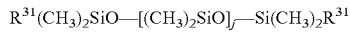

(in the formula, $R^{31}$ independently represents a methyl group or a hydroxy group, and j is a number of from 1 to 20,000).

Average particle diameter of dispersion particle in dimethylpolysiloxane is preferably less than 100 μm, more preferably 50 μm or less, and even more preferably 4 μm or less and further 2 μm or less. In terms of a feel upon use and conditioning effect, the average particle diameter of 0.1 μm or higher is preferable.

As an example of the dimethylpolysiloxane, commercially available products such as "SILICONE CF2450" manufactured by Dow Corning Toray Co., Ltd. which contains dimethylpolysiloxane oil (j is from 300 to 6,500) in an amount of 60% by weight and has average particle diameter of 0.8 and "SILICONE CF2460" manufactured by Dow Corning Toray Co., Ltd. which contains dimethylpolysiloxane oil (k is from 300 to 6,500) in an amount of 50% by weight and has average particle diameter of 50 μm, or "KHE-1" manufactured by Shin-Etsu Chemical Co., Ltd. can be used.

(II) Amino-Modified Silicone:
Various amino-modified silicones may be used. Those described in the third edition of CTFA dictionary (Cosmetic Ingredient Dictionary, USA) in the name of amodimethicone having average molecular weight of from 3,000 to 100,000 is preferable. Examples of the commercially available product include SM 8704C (manufactured by Dow Corning Toray Co., Ltd.), DC 929 (manufactured by Dow Corning), KT 1989 (manufactured by Momentive Performance Materials Inc.), 8500 Conditioning Agent, DOW CORNING TORAY SS-3588, and DOW CORNING TORAY SILSTYLE 104 (manufactured by Dow Corning Toray Co., Ltd.), and the like.

(III) Other Silicones:
In addition to above, polyether-modified silicone, methylphenylpolysiloxane, fatty acid-modified silicone, alcohol-modified silicone, alkoxy-modified silicone, epoxy-modified silicone, fluorine-modified silicone, cyclic silicone, and alkyl-modified silicone, and the like can be mentioned.

The silicones may be used in combination of two or more types. From the viewpoint of smoothness from washing to rinsing hair, the content is preferably from 0.01 to 10% by weight, more preferably from 0.05 to 5% by weight, and even more preferably from 0.1 to 3% by weight in the aqueous hair cleansing agent.

For a case where the cleansing composition of the present invention is an aqueous hair cleansing agent, a pearlescent agent including ethylene glycol monofatty acid ester, ethylene glycol difatty acid ester, ethylene glycol monoalkyl ether, or ethylene glycol dialkyl ether may be contained.

Examples of the ethylene glycol monofatty acid ester include ethylene glycol monostearic acid ester, and ethylene glycol monobehenic acid ester, and the like, examples of the ethylene glycol difatty acid ester include ethylene glycol distearyl ester (in the Examples below (that is, Table 3), it is described as "ethylene glycol distearyl"), ethylene glycol dibehenyl ester, and the like. Examples of the ethylene glycol monoalkyl ether include ethylene glycol monostearyl ether, and the like. Examples of the ethylene glycol dialkyl ether include ethylene glycol distearyl ether, and the like.

They may be used in combination of two or more types, and the content is preferably from 0.1 to 10% by weight, more preferably from 0.2 to 5% by weight, and even more preferably from 0.5 to 4% by weight in the aqueous hair cleansing agent of the present invention, in terms of increasing storage stability of the aqueous hair cleansing agent and smoothness during bubbling and rinsing.

For a case in which the cleansing composition of the present invention is an aqueous hair cleansing agent, it may comprise an oily agent as the other conditioning agent. Examples of the oily agent include hydrocarbons such as squalene, squalane, liquid paraffin, liquid isoparaffin, and cycloparaffin; glycerides such as castor oil, cacao oil, mink oil, avocado oil, olive oil, sunflower oil, and camellia oil; waxes such as beeswax, whale wax, lanolin, and carnauba wax; alcohols such as cetyl alcohol, oleyl alcohol, stearyl alcohol, isostearyl alcohol, 2-octyldodecanol, glycerin, myristyl alcohol, behenyl alcohol, and cetostearyl alcohol; esters such as isopropyl palmitate, isopropyl myristate, octyl dodecyl myristate, hexyl laurate, cetyl lactate, propylene glycol monostearate, oleyl oleate, hexadecyl 2-ethylhexanoate, isononyl isononanoate, tridecyl isononanoate; higher fatty acids such as capric acid, lauric acid, myristic acid, palmitic acid, stearic acid, behenic acid, oleic acid, coconut fatty acid, isostearic acid, and isopalmitic acid; and also isostearyl glyceryl ether and polyoxypropylene butyl ether, and the like. Among them, higher alcohols are preferable. Myristyl alcohol, cetyl alcohol, stearyl alcohol, sunflower oil, and camellia oil are more preferable.

The oily agent may be used either singly or in combination of two or more types. Content is preferably from 0.001 to 2% by weight, more preferably from 0.005 to 1.5% by weight, and even more preferably from 0.01 to 1% by weight in the aqueous hair cleansing agent of the present invention.

The aqueous hair cleansing agent may comprise a viscosity adjuster. Examples of the viscosity adjuster include hydroxyethyl cellulose, methyl cellulose, polyethylene glycol, polypropylene glycol, ethylene glycol, propylene glycol, isoprene glycol, ethanol, benzyl alcohol, benzyloxy ethanol, phenoxy ethanol, clay mineral, and salts (sodium chloride, ammonium chloride, sodium citrate, and the like), and the like. Among them, benzyl alcohol, ethanol, polypropylene glycol, sodium chloride and sodium citrate are preferable. Two or more types of the viscosity adjuster may be used in combination. In addition, the use amount is preferably from 0.01 to 5% by weight, more preferably from 0.05 to 4% by weight, and even more preferably from 0.1 to 3% by weight in the aqueous hair cleansing agent of the present invention, in terms of foam volume and foam quality.

In the aqueous hair cleansing agent, components that are commonly used for an aqueous hair cleansing agent may be used in addition to the above components, depending on desired use. Examples of the optional components include an anti-dandruff agent; a vitamin agent; an anti-microbial agent; an anti-inflammatory agent such as glycyrrhizic acid, glycyrrhetinic acid, and derivatives thereof; a preservative; a chelating agent; a moisturizing agent such as sorbitol and pantenol; a colorant such as pigment and dye; extracts such as a polar solvent extract of eucalyptus, proteins obtained from sea shell having a pearlescent layer or pearl, or hydrolysates thereof, proteins obtained from honey bee, royal jelly, and silk, or hydrolysates thereof, protein-containing extract from seeds of a leguminous plant, Asian ginseng extract, rice germ extract, fucoid extract, aloe extract, lotus flower extract, pomegranate extract, rosa multiflora extract, chamomile extract, licorice extract, *Alpinia zerumbet* extract, chlorella extract; a pearlescent agent such as titanium oxide, other than those described above; fragrance; an UV absorbing agent; an anti-oxidant; Shea butter, rose water, orange oil, and eucalyptus oil, and the like.

The aqueous hair cleansing agent is prepared by combining the components (A) to (C) with the other components and dissolving them in water.

pH upon application of the aqueous hair cleansing agent to hair is, from the viewpoint of enhancing shine or manageability of hair, preferably from 2 to 5, and more preferably from 3 to 4.5 (after diluted with water to 20 times by weight, 25° C.)

The pH adjuster is selected from hydroxy monocarboxylic acid and dicarboxylic acid. Specific examples of the hydroxy monocarboxylic acid include glycolic acid, lactic acid, glycerin acid, gluconic acid, and panthotenic acid, and the like. Specific examples of the dicarboxylic acid include malic acid, oxalic acid, malonic acid, maleic acid, succinic acid, and glutaric acid, and the like. From the viewpoint of increasing lathering in acidic region by using the components (A), (B), and (C) in combination, glycolic acid, lactic acid, and malic acid are more preferable.

The carboxylic acid may be used in combination of two or more types. Content of the carboxylic acid is preferably 0.01 to 5% by weight, more preferably from 0.1 to 3% by weight, and even more preferably from 0.3 to 2% by weight in the aqueous hair cleansing agent of the present invention.

Meanwhile, in addition to the hydroxycarboxylic acid, an aromatic carboxylic acid such as benzoic acid may be used.

Further, as another pH adjuster, a base such as sodium hydroxide, potassium hydroxide, and ammonium chloride may be used in combination of an organic acid.

A form of the aqueous hair cleansing agent can be suitably selected from a liquid, a gel, and the like, and water and lower alcohol may be used in addition to water as a solvent.

When the cleansing composition of the present invention is a skin cleansing agent, it may be produced by adding each component in order into water and dissolving them by fully stirring at from 20 to 70° C., although it is not specifically limited thereto. When a powdery polymer is mixed, it is preferable that the polymer be first dispersed in water and then each component be mixed with each other.

When the cleansing composition of the present invention is a skin cleansing agent, it preferably has pH of from 5 to 10, and more preferably pH of from 5.7 to 9.1 at 30° C. pH is measured after diluted with water to 20 times by weight.

Method for producing the aqueous hair cleansing agent comprises, although it is not specifically limited thereto, a step of obtaining cationized hydroxypropyl cellulose as the component (C) by the method including the first and the second steps described above, and a step of mixing the component (C) obtained from the previous step, the component (A), and the component (B) with water.

In the aqueous hair cleansing agent, by using the component (A) to (C) in combination, sufficient foam volume allowing ease of movement of hands and fingers even in damaged hair and light foam quality are obtained, and also foam dissipation is favorable, thus the residual feel during rinsing is suppressed. Although the reason is not exactly clear, it is believed that, by the coacervation of the component (A) and the component (C) during rinsing, complexes are precipitated on hair surface so that the component (C) can remain even after rinsing. It is also believed that, as the component (C), the component (A), and the component (B) present on hair surface make a suitable foam quality for hair washing, good lathering property, ease of movement of hands or fingers even when applied to damaged hair, and an effect of suppressing residual feel during rinsing are obtained.

The cleansing composition of the present invention can be applied as a skin cleansing agent such as hand soap, hand wash, facial wash, cleansing foam, and body cleansing agent such as body soap, and also a hair cleansing agent such as shampoo. It is also preferred as a skin cleansing agent for body. It is also preferred as an aqueous hair cleansing agent.

The method for cleansing skin by using the cleansing composition of the present invention is, for example, as follows. Specifically, the cleansing composition of the present invention is applied in an appropriate amount to a body, that is, a skin of human body such as face, hand or feet, and torso, allowed to bubble for cleansing, and rinsed off using hot water by shower, and the like. It is also possible that a suitable amount is added onto a cleansing aid such as towel, sponge, and brush and allowed to bubble for cleansing.

With regard to the embodiments described above, the present invention also discloses the following composition, method, and use.

<1> A cleansing composition comprising the following components (A), (B), (C), and (D):

(A) from 3 to 40% by weight of an anionic surfactant, (B) from 0.01 to 5% by weight of a glyceryl ether having an alkyl group or alkenyl group with from 4 to 12 carbon atoms, (C) from 0.01 to 10% by weight of a cationized hydroxypropyl cellulose represented by the following formula (1),

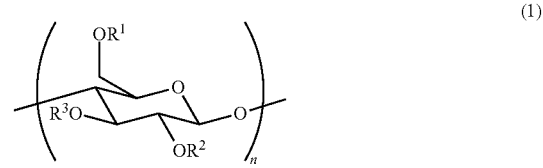

(1)

wherein $R^1$, $R^2$ and $R^3$ each independently represent a substituent having a cationized ethyleneoxy group and a propyleneoxy group that are represented by the following formula (2) or (3), and n represents a number of from 20 to 5000 which represents an average polymerization degree of anhydroglucose, in which substitution degree of the cationized ethyleneoxy group is from 0.01 to 3 and substitution degree of the propyleneoxy group is from 0.01 to 5),

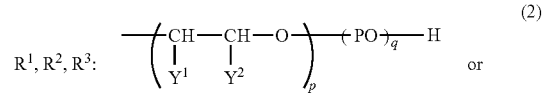

(2)

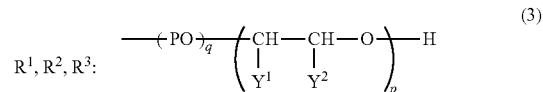

(3)

wherein one of $Y^1$ and $Y^2$ represents a hydrogen atom and the other is a cationic group represented by the following formula (4), PO represents a propyleneoxy group, p represents a number of the cationized ethyleneoxy group (—CH($Y^1$)—CH($Y^2$)—O—) contained in the formula (2) or (3), q represents a number of the propyleneoxy group (—PO—) in the formula (2) or (3), each representing 0 or a positive number, in which, when none of p and q is 0, the cationized ethyleneoxy group and propyleneoxy group may be added in any order, and when at least one selected from p and q is 2 or higher, it may be any one of a block bond or a random bond)

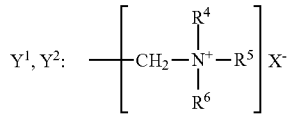

wherein $R^4$, $R^5$ and $R^6$ each independently represent a linear or branched alkyl group having from 1 to 3 carbon atoms, and $X^-$ represents an anionic group, and (D) water.

<2> A cleansing composition comprising the following components (A), (B), (C), (D), and (E):

(A) from 3 to 40% by weight of an anionic surfactant, (B) from 0.01 to 5% by weight of a glyceryl ether having an alkyl group or alkenyl group with from 4 to 12 carbon atoms, (C) from 0.01 to 10% by weight of a cationized hydroxypropyl cellulose represented by the following formula (1),

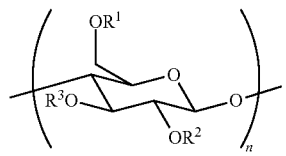

wherein $R^4$, $R^2$ and $R^3$ each independently represent a substituent having a cationized ethyleneoxy group and a propyleneoxy group that are represented by the following formula (2) or (3), and n represents a number of from 20 to 5000 which represents an average polymerization degree of anhydroglucose, in which substitution degree of the cationized ethyleneoxy group is from 0.01 to 3 and substitution degree of the propyleneoxy group is from 0.01 to 5,

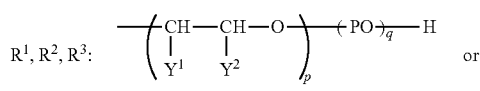

or

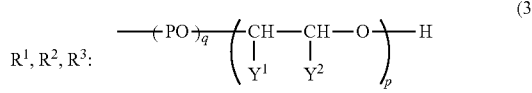

wherein one of $Y^1$ and $Y^2$ represents a hydrogen atom and the other is a cationic group represented by the following formula (4), PO represents a propyleneoxy group, p represents the number of the cationized ethyleneoxy group (—CH($Y^1$)—CH($Y^2$)—O—) in the formula (2) or (3), q represents the number of the propyleneoxy group (—PO—) in the formula (2) or (3), each representing 0 or a positive number, in which, when none of p and q is 0, the cationized ethyleneoxy group and propyleneoxy group may be added in any order, and when at least one selected from p and q is 2 or higher, it may be any one of a block bond or a random bond)

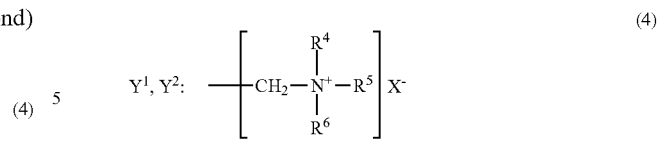

wherein $R^4$, $R^5$ and $R^6$ each independently represent a linear or branched alkyl group having from 1 to 3 carbon atoms, and $X^-$ represents an anionic group), (D) water, and (E) from 0.01 to 4% by weight of one or two or more selected from (E1) a cationic polymer, (E2) an anionic polymer, (E3) a non-ionic polymer and (E4) an amphoteric polymer.

<3> The cleansing composition described in above <1> or <2>, in which the component (A) is at least one selected from polyoxyalkylene alkyl ether sulfate, fatty acid salt, alkyl ether carboxylate, N-acylamino acid salt and N-acylalkyl taurine salt, preferably alkyl ether carboxylate, N-acylamino acid salt, or N-acylalkyl taurine salt, and also combination of alkyl ether carboxylate and polyoxyalkylene alkyl ether sulfate, combination of alkyl ether carboxylate and fatty acid salt, or combination of alkyl ether carboxylate and polyoxyalkylene alkyl ether sulfate and fatty acid salt.

<4> The cleansing composition described in any one of above <1> to <3>, in which the component (B) is isodecyl glyceryl ether or 2-ethylhexyl glyceryl ether, and preferably 2-ethylhexyl glyceryl ether.

<5> The cleansing composition described in any one of above <1> to <4>, in which, for the component (C), the average polymerization degree n in the formula (1) is 20 or higher, preferably 100 or higher, and more preferably 400 or higher, and also 5000 or lower, preferably 2000 or lower, and more preferably 1300 or lower, the substitution degree of the cationized ethyleneoxy group is 0.01 or higher, preferably 0.1 or higher, and more preferably 0.18 or higher, and also 3 or lower, preferably 2.4 or lower, and more preferably 3 or lower, and the substitution degree of the propyleneoxy group is 0.01 or higher, preferably 0.2 or higher, and more preferably 1.1 or higher, and also 5 or less, preferably 3 or less, and more preferably 2.9 or less.

<6> The cleansing composition described in any one of above <2> to <5>, in which (E1) cationic polymer is at least one selected from diallyl dialkyl quaternary ammonium salt (DMDAAC)/acrylamide (AM) copolymer, cationized cellulose (O-[2-hydroxy-3-(trimethylammonio)propyl]hydroxyethyl cellulose chloride)], and cationized guar gum (guar hydroxypropyl triammonium chloride)], and preferably diallyl dialkyl quaternary ammonium salt (DMDAAC)/acrylamide (AM) copolymer, (E2) anionic polymer is at least one selected from alkyl acrylate alkyl methacrylate.polyoxyethylene (20) stearyl ether copolymer (INCI: ACRYLATES/STEARETH-20 METHACRYLATE COPOLYMER), alkyl acrylate.alkyl methacrylate.polyoxyethylene (25) lauryl ether copolymer (INCI: ACRYLATES/LAURETH-25 METHACRYLATE COPOLYMER), alkyl acrylate alkyl methacrylate.polyoxyethylene (25) behenyl ether copolymer (INCI: ACRYLATES/BEHENETH-25 METHACRYLATE COPOLYMER), and acrylic acid.alkyl methacrylate copolymer (INCI: ACRYLATES/C10-30 ALKYL ACRYLATE CROSSPOLYMER) and preferably acrylic acid.alkyl methacrylate copolymer (INCI: ACRYLATES/C10-30 ALKYL ACRYLATE CROSSPOLYMER), (E3) non-ionic polymer is at least one selected from hydroxyethyl cellulose, hydroxypropylmethyl cellulose, hydroxypropyl guar gum, polyvinyl pyrrolidone, and polyethylene glycol, and preferably hydroxypropyl guar gum, or polyethylene glycol, and (E4) amphoteric polymer is a copolymer of dimethyl diallyl ammonium chloride, acrylic acid, and acrylamide.

<7> The cleansing composition described in any one of above <1> to <6>, in which a content of the component (A) is from 3 to 40% by weight in the total composition of the cleansing agent, and in case of a skin cleansing agent, it is 3% by weight or more, preferably 5% by weight or more, and more preferably 7% by weight or more, and also 40% by weight or less, preferably 20% by weight or less, and more preferably 15% by weight or less in the total composition.

<8> The cleansing composition described in any one of above <1> to <7>, in which a content of the component (B) is from 0.01 to 10% by weight in the total composition of the cleansing agent, and in case of a skin cleansing agent, it is 0.02% by weight or more, preferably 0.2% by weight or more, and more preferably 0.4% by weight or more, and also 5% by weight or less, preferably 2% by weight or less, and more preferably 1.2% by weight or less in the total composition.

<9> The cleansing composition described in any one of above <1> to <8>, in which a content of the component (C) is from 0.01 to 10% by weight in the total composition of the cleansing agent, and in case of a skin cleansing agent, it is 0.01% by weight or more, preferably 0.2% by weight or more, and more preferably 0.5% by weight or more, and also 10% by weight or less, preferably 2% by weight or less, and more preferably 1.4% by weight or less in the total composition.

<10> The cleansing composition described in any one of above <1> to <9>, in which a content of the component (D) is from 40 to 90% by weight in the total composition.

<11> The cleansing composition described in any one of above <2> to <10>, in which a content of the component (E) is from 0.01 to 4% by weight, preferably from 0.1 to 2.1% by weight, and more preferably from 0.3 to 1.4% by weight in the total composition.

<12> The cleansing composition described in any one of above <2> to <11>, in which the weight ratio between the components (E1) and (C), (E1)/(C), is from 0.1 to 5, and preferably from 0.2 to 2.

<13> The cleansing composition described in any one of above <2> to <12>, in which the weight ratio between the components (E2) and (C), (E2)/(C), is from 0.1 to 5, and preferably from 0.2 to 2.

<14> The cleansing composition described in any one of above <1> to <13>, further comprising at least one (F) non-ionic surfactant selected from alkyl polyglycoside-based non-ionic surfactant and polyoxyethylene alkyl ether-based non-ionic surfactant.

<15> The cleansing composition described in above <14>, in which the component (F) is a non-ionic surfactant having HLB of from 10 to 20, and preferably HLB of from 13 to 16.

<16> The cleansing composition described in above <14> or <15>, in which the component (F) is at least one selected from polyoxyethylene (21) lauryl ether (HLB 14), polyoxyethylene (20) 2-hexyldecyl ether (HLB 14), polyoxyethylene (20) octyl dodecyl ether (HLB 13), and polyoxyethylene (16) lauryl ether (HLB 15.8), and is preferably, polyoxyethylene (16) lauryl ether.

<17> The cleansing composition described in any one of above <14> to <16>, in which the component (F) is at least one selected from alkyl (C10-16) polyglucoside and alkyl (C9-11) glucoside.

<18> The cleansing composition described in any one of above <14> to <17>, in which a content of the component (F) is from 0.05 to 10% by weight, preferably from 0.2 to 6% by weight, and more preferably from 0.5 to 4% by weight in the total composition of the cleansing agent.

<19> The cleansing composition described in any one of above <1> to <18>, further comprising (G) amphoteric surfactant.

<20> The cleansing composition described in above <19>, in which a content of the component (G) is from 0.1 to 10% by weight, and preferably from 0.5 to 6% by weight in the total composition of the cleansing agent.

<21> The cleansing composition described in any one of above <1> to <20>, which is a skin cleansing agent.

<22> A method for cleansing a skin comprising applying the cleansing composition described in any one of above <1> to <21> to a skin of human body for cleansing, followed by rinsing.

<23> Use of the cleansing composition described in any one of above <1> to <20> for production of a skin cleansing agent.

<24> Use of the cleansing composition described in any one of above <1> to <20> for production of an aqueous hair cleansing agent.

<25> An aqueous hair cleansing agent comprising the following components (A), (B), (C), and (D):

(A) an anionic surfactant, (B) a monoalkyl glyceryl ether or monoalkenyl glyceryl ether having an alkyl group with from 4 to 12 carbon atoms or alkenyl group with from 4 to 12 carbon atoms, (C) a cationized hydroxypropyl cellulose, and (D) water, in which the component (C) has a main chain derived from anhydroglucose represented by the following formula (1), substitution degree of the cationized ethyleneoxy group is from 0.01 to 2.9, and substitution degree of the propyleneoxy group is from 0.1 to 4.0.

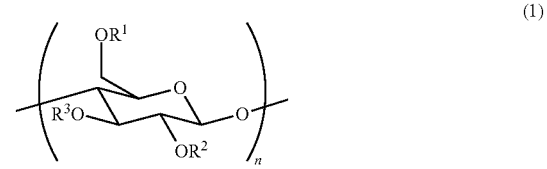

wherein in the above formula (1), $R^1$, $R^2$ and $R^3$ each independently represent a substituent having a cationized ethyleneoxy group and a propyleneoxy group that are represented by the following formula (2), and n represents the average polymerization degree of anhydroglucose and n is from 50 to 5000

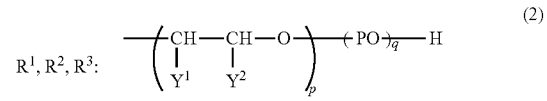

wherein in the above formula (2), one of $Y^1$ and $Y^2$ represents a hydrogen atom and the other is a cationic group represented by the following formula (4), PO represents a propyleneoxy group, p represents the number of the cationized ethyleneoxy group ($-CH(Y^1)-CH(Y^2)-O-$) in the formula (2), q represents the number of the propyleneoxy group (—PO—) in the formula (2), each representing 0 or a positive number, with the proviso that none of p and q is 0 for all $R^1$, $R^2$ and $R^3$, and, when none of p and q is 0, the cationized ethyleneoxy group and propyleneoxy group may be added in any order, and when none of p and q is 0 and at least one selected from p and q is 2 or higher, it may be any one of a block bond or a random bond

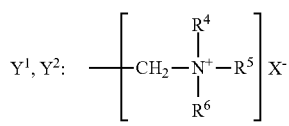

(4)

wherein in the above formula (4), $R^4$, $R^5$ and $R^6$ each independently represent a linear or branched alkyl group having from 1 to 3 carbon atoms, and $X^-$ represents an anionic group.

<26> The aqueous hair cleansing agent described in above <25>, in which a content of the component (C) is from 0.01 to 10% by weight in the total aqueous hair cleansing agent.

<27> The aqueous hair cleansing agent described in above <25> or <26>, in which the weight ratio of the component (C) to the component (A), (C)/(A), is from 0.0005 to 0.5.

<28> The aqueous hair cleansing agent described in any one of above <25> to <27>, in which the weight ratio of the component (C) to the component (B), the component (C)/the component (B), is from 0.002 to 50.

<29> The aqueous hair cleansing agent described in any one of above <25> to <28>, in which a content of the component (A) is from 3 to 20% by weight in the total aqueous hair cleansing agent.

<30> The aqueous hair cleansing agent described in any one of above <25> to <29>, in which a content of the component (B) is from 0.01 to 5% by weight in the total aqueous hair cleansing agent.

<31> The aqueous hair cleansing agent described in any one of above <25> to <30>, in which a content of the component (A) is from 5 to 18% by weight, a content of the component (C) is from 0.02 to 5% by weight, and a content of the component (B) is from 0.05 to 4% by weight.

<32> The aqueous hair cleansing agent described in any one of above <25> to <31>, in which the component (A) is at least one selected from the compounds represented by the following formula (11):

$$R^{11}O(CH_2CH_2O)_uSO_3M \quad (11)$$

wherein in the formula (11), $R^{11}$ represents an alkyl group or alkenyl group having from 10 to 18 carbon atoms, M represents an alkali metal, an alkali earth metal, ammonium, alkanolamine, or a basic amino acid, and u represents a number of from 0.5 to 5 in weight average.

<33> The aqueous hair cleansing agent described in any one of above <25> to <32>, in which the component (B) is monoalkyl glyceryl ether or monoalkenyl glyceryl ether having an alkyl group with from 8 to 10 carbon atoms or an alkenyl group with from 8 to 10 carbon atoms.

<34> The aqueous hair cleansing agent described in any one of above <25> to <33>, in which, for any one of $R^1$, $R^2$ and $R^3$ in the formula (1), p and q in the formula (2) is 0 or 1.

<35> The aqueous hair cleansing agent described in any one of above <25> to <34>, in which, for any one of $Y^1$ and $Y^2$ in the formula (2), $R^4$, $R^5$ and $R^6$ in the formula (4) independently represent a methyl group or an ethyl group.

<36> The aqueous hair cleansing agent described in any one of above <25> to <35>, in which pH when diluted with water to 20 times by weight (25° C.) is from 2 to 5.

<37> The aqueous hair cleansing agent described in any one of above <25> to <36>, further comprising hydroxy monocarboxylic acid or dicarboxylic acid in an amount of from 0.01 to 5% by weight.

<38> The aqueous hair cleansing agent described in any one of above <25> to <37>, in which the component (C) is cationized hydroxypropyl cellulose obtained by a production method comprising the following first step and second step:

first step: low-crystallization is performed by crusher treatment after adding a cationizing agent to pulp, and then a reaction between the pulp and cationizing agent is allowed to occur to obtain cationized cellulose while performing low-crystallization by crusher treatment after adding a base, and second step: the cationized cellulose obtained from the first step is reacted with propylene oxide to give cationized hydroxypropyl cellulose.

In the following Examples, methods for measuring various physical properties are as follows.

(1) Measurement of Moisture Contents in Pulp and Powdery Cellulose:

Moisture contents in pulp and powdery cellulose were measured by using an infrared moisture tester ("FD-610", manufactured by Kett Electric Laboratory). The time point at which the weight change ratio is 0.1% or less for 30 seconds at measurement temperature of 120° C. was taken as the terminal measurement point.

(2) Calculation of Crystallinity of Pulp and Powdery Cellulose

By using "Rigaku RINT 2500VC X-RAY diffractometer" manufactured by Rigaku Corporation, calculation was made on the basis of the following equation (1) from the peak intensity of diffraction spectrum which has been measured in accordance with the following conditions.

X ray source: Cu/Kα-radiation, tube voltage: 40 kV, tube current: 120 mA

Measurement range: 2θ=from 5 to 45°

Measurement sample: prepared by compressing a pellet with area 320 mm²×thickness 1 mm X ray scan speed: 10°/min If the obtained crystallinity has a negative value, it was all regarded as crystallinity of 0%.

$$\text{Crystallinity (\%)} = [(I_{22.6} - I_{18.5})/I_{22.6}] \times 100 \quad (1)$$

(in the equation, $I_{22.6}$ indicates diffraction intensity of lattice plane (002 plane) (diffraction angle 2θ=22.6°), and $I_{18.5}$ indicates diffraction intensity of an amorphous part (diffraction angle 2θ=18.5°), in X ray diffraction).

(3) Calculation of Substitution Degrees of Cationized Ethyleneoxy Group and Propyleneoxy Group in Cationized Hydroxypropyl Cellulose (C-HPC):

After purifying C-HPC obtained from the Preparation Example by using a dialysis membrane (molecular weight cut off 1000), the aqueous solution was subjected to freeze-drying to give purified C-HPC. Chlorine content (%) in the obtained purified C-HPC was measured by elemental analysis and, by approximating that the number of cationic groups is the same as the number of chloride ions as a counter ion that are contained in C-HPC, amount (a (mol/g)) of the cationized ethyleneoxy group (—CH(Y1)-CH(Y2)O—) contained in the unit weight of C-HPC was calculated on the basis of the following equation (2).

$a$(Mol/g)=Chloride content obtained by elemental analysis (%)/(35.5×100) (2)

Except that the subject for analysis was purified C-HPC instead of hydroxypropyl cellulose, content (%) of hydroxypropoxy group was measured in accordance with the "Method for analysis of hydroxypropyl cellulose" described in Japanese Pharmacopoeia. Based on the following equation (3), content of hydroxypropoxy group (b mol/g) was calculated [formula weight ($OC_3H_6OH$=75.09].

$b$(Mol/g)=Content (%) of hydroxypropoxy group obtained by gas chromatography analysis/ (75.09×100)

With the obtained values a and b and also the following equations (4) and (5), substitution degree (k) of cationized ethyleneoxy group and substitution degree (m) of propyleneoxy group were calculated.

$$a=k/(162+k \times K+m \times 58) \quad (4)$$

$$b=m/(162+k \times K+m \times 58) \quad (5)$$

[in the formula, k and K represent the substitution degree and the formula weight, respectively, of a cationized ethyleneoxy group, and m represents the substitution degree of a propyleneoxy group].

(4) Calculation of Water Soluble Fractions:

Sample (0.50 g) was weighed in a 50 mL screw tube, 49.5 g of ion exchange water was added, and dissolved by stirring for 12 hours with a magnetic stirrer. The solution was transferred to a 50 mL centrifuge tube, and centrifuged for 20 minutes at 3000 rpm (2000×g). The supernatant (5 mL) was dried under reduced pressure (105° C., 3 hours) to give the solids, and the water soluble fraction was calculated in accordance with the following equation.

Water soluble fraction (%)=(Solids weight in 5 mL supernatant (g)×10/Sample weight)×100

(5) Measurement of Average Polymerization Degree (Copper Ammonia Method):

(5-1) Measurement of Viscosity Average Polymerization Degree of Pulp and Powdery Cellulose;

(i) Preparation of Solution for Measurement;

To a measuring flask (100 mL), copper (I) chloride (0.5 g) and 25% ammonia water (from 20 to 30 mL) were added. After complete dissolution, copper (II) hydroxide (1.0 g) and 25% ammonia water were added until it was right below the marked line. The resultant was stirred for from 30 to 40 minutes for complete dissolution. After that, precisely weighed cellulose was added and the ammonia water was filled up to the marked line. It was sealed to protect against air and stirred for 12 hours with a magnetic stirrer for dissolution. As a result, a solution for measurement was prepared. The addition amount of cellulose was changed in the range of from 20 to 500 mg to prepare a solution for measurement with different concentration.

(ii) Measurement of Viscosity Average Polymerization degree;

The solution for measurement obtained from above (i) (copper ammonia solution) was applied to an Ubbelohde viscometer. After keeping in a thermostat bath (20±0.1° C.) for 1 hour, the liquid flow rate was measured. From the flow rate (t (sec)) of copper ammonia solution with various cellulose concentrations (g/dL) and flow rate (t0 (sec)) of aqueous copper ammonia solution to which cellulose has not been added, the reduced viscosity ($\eta sp/c$) at each concentration was calculated in accordance with the following equation.

$$(\eta sp/c)=\{(t-t0)/t0\}/c$$

(c: cellulose concentration (g/dL)

Further, by extrapolating the reduced viscosity to c=0, intrinsic viscosity [$i$] (dL/g) was obtained and the viscosity average polymerization degree (DP) was obtained in accordance with the following formula.

$$DP=2000 \times [\eta]$$

(5-2) Measurement of Viscosity Average Polymerization Degree of C-HPC;

(iii) Preparation of Solution for Measurement;

Except that precisely weighed C-HPC was used instead of precisely weighed cellulose, a solution for measurement was prepared in the same manner as the preparation of a solution for measurement described in the above (i).

(iv) Measurement of Viscosity Average Polymerization Degree;

Except that cellulose equivalent concentration (g/dL) was employed as concentration of a solution for measurement, the measurement was performed in the same manner as the measurement of viscosity average polymerization degree described in above (ii).

As described herein, the cellulose equivalent concentration (ccell) indicates the weight (g) of the cellulose skeleton contained in 1 dL of the solution for measurement, and it is defined by the following equation (6).

$$ccell=u \times 162/(162+k \times K+m \times 58) \quad (6)$$

[in the equation, u indicates the weight (g) of weighed C-HPC which has been used for preparation of a solution for measurement, and k, K, and m each are the same as defined in the equation (4) and the equation (5)].

[Substitution Degree of Propyleneoxy Group (—PO—)]

Except that the subject for analysis was C-HPC obtained after purification using a dialysis membrane and freeze-drying instead of hydroxypropyl cellulose, substitution degree of propyleneoxy group was measured according to the method for analysis of hydroxypropyl cellulose described in Japanese Pharmacopoeia.

Preparation Example 1

Preparation of C-HPC (1)

(1) Chipping Step:

Sheet-shape wood pulp (manufactured by Tembec, average polymerization degree of 1770, crystallinity of 74%, and moisture content of 8.5%) was formed in a chip shape after treatment using a sheet pelletizer ("SGG-220", manufactured by HORAI Co, Ltd.).

(2) Step for Lowering Crystallinity by Mechanical Force after Adding Cationizing Agent:

The obtained chip-shape pulp (2.1 kg) and glycidyl trimethyl ammonium chloride (hereinafter, also referred to as "GMAC", manufactured by Sakamoto Yakuhin Kogyo Co., Ltd., moisture content of 20%, and purity of 90% or higher) (1.2 kg) (0.5 mol per mol of AGU) were mixed with each other in a bag, and then supplied to a batch type vibration mill ("FV-20" manufactured by CHUG KAKOHKI Co., Ltd.: total vessel volume 68.9 L, 114 rods made of SUS304, in which each rod has φ of 30 mm, length of 590 mm, and round cross section, and filling ratio of 70%). By performing a treatment for lowering crystallinity for 12 minutes at frequency of 20 Hz, total amplitude of 8 mm, and temperature of 30° C. or lower, a powdery mixture of cellulose and GMAC (moisture content of 22.3% relative to cellulose, viscosity average polymerization degree of 1350, and crystallinity of 68%) was obtained.

(3) Step for Adding Base Compound and Lowering Crystallinity with an Aid of Mechanical Force To the powdery mixture obtained from the step (2), NaOH powder (0.284 kg, 0.6 mol per mol of AGU) was added and subjected to a treatment for lowering crystallinity for 20 minutes using a batch type vibration mill at frequency of 20 Hz, total amplitude of 8 mm, and temperature of 50° C. or lower to obtain a powdery mixture of cationized cellulose (hereinafter, also referred to as "C-Cell"), GMAC, and NaOH. Further, polypropylene glycol (manufactured by Wako Pure Chemical Industries, Ltd., trade name; "polypropylene glycol diol type average molecular weight of 1000" (PPG1000); weight average molecular weight of 1000) 0.192 kg (10% by weight per raw material cellulose used in the step a)) was added to a batch type vibration mill for a treatment of lowering crystallinity for 120 minutes at frequency of 20 Hz, total amplitude of 8 mm, and temperature of 50° C. or lower to give powdery mixture (3.7 kg) of C-Cell, GMAC, NaOH, and PPG1000.

(4) Hydroxypropylation Reaction and Neutralization Step:

Powdery mixture (10.0 kg) prepared by repeating several times the step (2) and the step (3) was added to a Pro Share mixer (75 L). After increasing the internal temperature to 56° C., 2.8 kg of propylene oxide (1.5 mol per mol of AGU) was sequentially added dropwise so that the reaction was performed until the internal pressure decreases by consumption of propylene oxide. To 12.6 kg of the reaction product, 8.0 kg of 24% aqueous solution of lactic acid was added by spraying to give 20.6 kg of neutralization product.

The obtained neutralization product (15.2 kg) was added to a 65 L high speed mixer and dried under reduced pressure at internal temperature of from 70 to 80° C. to obtain the dry product (10.0 kg). The resulting dry product was pulverized by a pin mill and used as a powder.

The product was purified using a dialysis membrane (molecular weight cut off: 1000), and the aqueous solution was subjected to freeze-drying to give purified C-HPC (1). As a result of the analysis of the purified product, substitution degrees of the cationic group and propyleneoxy group were found to be 0.22 and 1.13, respectively. Further, the viscosity average polymerization degree of the obtained C-HPC (1) was found to be 693.

Preparation Example 2

Preparation of C-HPC (2)

(1) Chipping Step:

Sheet-shape wood pulp (Biofloc HV+ manufactured by Tembec, average polymerization degree of 1481, crystallinity of 74%, and moisture content of 4.6%) was formed in a chip shape (from 3 to 5 mm square) after treatment using a sheet pelletizer ("SGG-220", manufactured by HORAI Co, Ltd.).

(2) Step for Obtaining Alkali Cellulose

The chip-shape pulp (100 g) obtained from the above step (1) and 23.6 g of 0.7 mm particulate NaOH (equivalent to 1.0 mol per mol of AGU) were supplied to a batch type vibration mill ("MB-1" manufactured by CHUG KAKOHKI Co., Ltd.: total vessel volume of 3.5 L, 13 rods made of SUS304, in which each rod has φ of 30 mm, length of 218 mm, and round cross section, and filling ratio of 57%). After performing pulverizing treatment for 15 minutes (frequency of 20 Hz, amplitude of 8 mm, and temperature of from 30 to 70° C.), the resulting cellulose.NaOH mixture pulverized product was transferred to a mortar, and 50 g of water was added by spraying. It was then mixed for 5 minutes at 20° C. using a pestle to give alkali cellulose (average polymerization degree: 1175, crystallinity: 280).

(3) Hydroxypropylation Reaction Step

The alkali cellulose obtained from the step (2) was added to a sealed reactor (manufactured by Ni to Koatsu, 1.5 L autoclave) and the inside of the reaction vessel was replaced with nitrogen. Subsequently, propylene oxide was sequentially added under stirring at constant inside vessel pressure of 0.05 MPa after increasing temperature to 50° C., followed by the reaction for 7 hours. The total addition amount of propylene oxide was 102 g (equivalent to 3.0 mol per mol of AGU).

(4) Cationizing Reaction Step:

The reaction mixture (30.0 g) obtained from the above step (3) was transferred to a mortar, and 9.30 g (equivalent to 0.50 mol per mol of AGU) of 65% aqueous solution of 3-chloro-2-hydroxypropyltrimethyl ammonium chloride (manufactured by Yokkaichi Chemical Co., Ltd.) was added, followed by stirring for 5 minutes. After transferring to a 150 mL glass bottle, the reaction was allowed to occur for 7 hours at 50° C. to give crude C-HPC.

The crude C-HPC powder (5.0 g) was collected and neutralized with lactic acid. For the purpose of obtaining substitution degrees of the propyleneoxy group and cationized ethyleneoxy group, the neutralization product was purified by using a dialysis membrane (molecular weight cut off: 1000) and the aqueous solution was subjected to freeze-drying to give purified C-HPC (2).

As a result of the analysis of the purified product, substitution degrees of the cationic group and propyleneoxy group were found to be 0.18 and 2.0, respectively. Further, the viscosity average polymerization degree of the obtained C-HPC (2) was found to be 693.

Preparation Example 3

Preparation of C-HPC (3)

(1) Chipping Step:

Sheet-shape wood pulp (Biofloc HV+ manufactured by Tembec, average polymerization degree of 1604, α-cellulose content of 93.0%, crystallinity of 74%, and moisture content of 7.0%) was formed in a chip shape (from 3 to 5 mm square) after treatment using a sheet pelletizer ("SGG-220", manufactured by HORAI Co, Ltd.).

The obtained chip-shape pulp was added to a vacuum dryer (product name: VO-402, manufactured by Advantec Toyo Kaisha, Ltd.) and dried for 2 hours at 105° C., 20 kPa under nitrogen stream to give a dry chip-shape pulp (average polymerization degree: 1604, α-cellulose content: 99.2%, crystallinity: 74%, and moisture content: 0.8%).

(2) Step for Obtaining Alkali Cellulose (Step 1)

The obtained dry chip-shape pulp (920 g) was supplied to a vibration rod mill ("FV-10" manufactured by CHUG KAKOHKI Co., Ltd.: total vessel volume of 35 L, 63 rods were used in which each rod has diameter of 30 mm). After performing pulverizing treatment for 10 minutes (20 Hz, amplitude of 8 mm, and temperature of from 10 to 40° C.), powdery pulp with lowered crystallinity (920 g, average polymerization degree: 1198, crystallinity: 14%, moisture content: 1.0%) was obtained as cellulose-containing raw material (I).

(Step 2)

Powdery pulp (460 g) obtained from above (step 1) as cellulose-containing raw material (I) was supplied to a mixer ("Redige mixer" with volume of 5 L, manufactured by MATSUBO Corporation), and while being stirred with main wing at 250 rpm and chopper wing at 2500 rpm, 42.5% aqueous solution of sodium hydroxide (266.8 g (equivalent to 1.0 mol per mol of AGU of cellulose in the cellulose-containing raw material (I) (hereinafter, also referred to as "raw material (II) cellulose), and 33% of water per raw material (II) cellulose)) was added for 1.5 minutes by spraying. After the spraying, the internal temperature was increased to 50° C. and aged under stirring for 3 hours to obtain an alkali cellulose mixture.

(3) Hydroxypropylation Reaction Step:

The alkali cellulose mixture (720.5 g) obtained from above (2) was added to a Redige mixer and the temperature was increased to 50° C. while being stirred with main wing at 50 rpm and chopper wing at 400 rpm. After that, propylene oxide (571.4 g, equivalent to 3.5 mol per mol of AGU of the alkali cellulose) was added dropwise thereto for 3.5 hours. Once the dropwise addition was completed, it was aged for 2 hours at 50° C.

(4) Cationizing Reaction and Neutralization Step:

The reaction mixture (272.0 g) obtained from the hydroxypropylation was added to a mixer ("High Speed Mixer" with 2 L volume, manufactured by Fukae Pautec, Co., Ltd.). After increasing the internal temperature to 50° C., 65% aqueous solution of 3-chloro-2-hydroxypropyltrimethyl ammonium chloride (manufactured by Yokkaichi Chemical Co., Ltd.) (82.8 g, equivalent to 0.5 mol per mol of AGU which constitutes the cellulose skeleton of the compound containing cellulose skeleton in the reaction mixture that has been obtained by hydroxypropylation) was added for 1.5 minutes by spraying while being stirred with main wing at 337 rpm and chopper wing at 1800 rpm. After spraying, aging under stirring was performed for 2 hours to give crude C-HPC. Subsequently, 29% aqueous solution of lactic acid was sprayed for 1.5 minutes for neutralization of the crude C-HPC.

The crude C-HPC powder (5.0 g) was collected. For the purpose of obtaining substitution degrees of the propyleneoxy group and cationized ethyleneoxy group, the neutralization product was purified by using a dialysis membrane (molecular weight cut off: 1000) and the aqueous solution was subjected to freeze-drying to give purified C-HPC (3).

As a result of the analysis of the purified product, substitution degrees of the cationic group and propyleneoxy group were found to be 0.11 and 2.0, respectively. Further, the viscosity average polymerization degree of the obtained C-HPC (3) was found to be 743.

Preparation Example 4

Preparation of C-HPC (4)

(1) Chipping Step:

As cellulose, sheet-shape wood pulp (manufactured by Tembec, viscosity average polymerization degree of 1770, crystallinity of 74%, and moisture content of 7.6%) was formed in a chip shape after treatment using a sheet pelletizer ("SGG-220", manufactured by HORAI Co, Ltd.).

(2) Step for Lowering Crystallinity by Mechanical Force after Adding Cationizing Agent:

The obtained chip-shape pulp (108 g) and glycidyl trimethyl ammonium chloride (hereinafter, also referred to as "GMAC", manufactured by Sakamoto Yakuhin Kogyo Co., Ltd., moisture content of 20%, and purity of 90% or higher) (23.4 g) (0.2 mol per unit mol of the anhydroglucose in cellulose (hereinafter, also referred to as "AGU")) were mixed with each other using a pestle and mortar, and then supplied to a batch type vibration mill ("MB-1" manufactured by CHUG KAKOHKI Co., Ltd.: total vessel volume of 3.5 L, 13 rods made of SUS304, in which each rod has $\phi$ of 30 mm, length of 218 mm, and round cross section, and filling ratio of 57%). By performing a treatment for lowering crystallinity for 12 minutes at frequency of 20 Hz, total amplitude of 8 mm, and temperature of 30° C. or lower, a powdery mixture (131 g) of cellulose and GMAC (moisture content of 12.3% relative to cellulose, viscosity average polymerization degree of 1350, and crystallinity of 68%) was obtained.

(3) Step for Lowering Crystallinity by Mechanical Force after Adding Base Compound:

The powdery pulp (131 g) obtained from above (2) was mixed with 24.7% aqueous sodium hydroxide solution (20 g, 0.2 mol per mol of AGU) using a pestle and mortar, and then supplied to a batch type vibration mill ("MB-1" manufactured by CHUO KAKOHKI Co., Ltd.: total vessel volume of 3.5 L, 117 rods made of SUS304, in which each rod has $\phi$ of 10 mm, length of 218 mm, and round cross section, and filling ratio of 57%). By performing a treatment for lowering crystallinity for 60 minutes at frequency of 20 Hz, total amplitude of 8 mm, and temperature of 30° C. or lower, a powdery mixture (151 g) of C-Cell, GMAC, and sodium hydroxide (moisture content of 27.4% to cellulose, viscosity average polymerization degree of 1330, and crystallinity of 45%) was obtained. The powdery mixture (5 g) was collected, neutralized with acetic acid, and washed three times with 85% aqueous solution of isopropyl alcohol (100 mL) for desalting and purification. Subsequently, by drying under reduced pressure, purified cationized cellulose (4 g, viscosity average polymerization degree: 1330, crystallinity: 45%) was obtained.

As a result of the elemental analysis, the substitution degree of cationic group was calculated to be 0.1. Further, the water soluble fraction was 31%.

(4) Hydroxypropylation Reaction, Neutralization Step:

The obtained cationized cellulose (100 g, non-neutralized and non-purified product) was injected to a 1 L kneader equipped with a reflux condenser (PNV-1 type, manufactured by IRIE SHOKAI Co., Ltd.). The jacket part of the kneader was heated to 70° C. by hot water, and propylene oxide (141.9 g, 6 mol per mol of AGU, manufactured by Kanto Chemical Co., Inc., special grade reagent) was added dropwise thereto under nitrogen atmosphere, and the reaction was performed for 40 hours until the reflux stops by consumption of propylene oxide.

The product was collected from the kneader to give crude C-HPC powder with pale brown color (240 g). 10.0 g of the reaction product was collected and neutralized with acetic acid to give a pale brown solid. The product was purified by using a dialysis membrane (molecular weight cut off: 1000) and the aqueous solution was subjected to freeze-drying to give purified C-HPC (4).

From the content of the propyleneoxy group [molecular weight (C3H60)=58.08] obtained by the hydroxypropyl cellulose analysis, a substitution degree of the propyleneoxy group was found to be 2.9. Further, the water soluble fraction of the obtained C-HPC (4) was found to be 71%, and the viscosity average polymerization degree was found to be 1,300.

Preparation Example 5

Preparation of C-HPC (5)

(1) Preparation of Dry Powder Cellulose:

Powder cellulose (manufactured by NIPPON PAPER Chemicals Co., Ltd., cellulose powder KC FLOCK W-400G, average polymerization degree: 191, crystallinity: 77%, and moisture content: 7.0%) was dried for 12 hours at 50° C. under reduced pressure to obtain dry powdery cellulose (moisture content: 1.0%).

(2) Cationizing Step (1):

The obtained powder cellulose (100 g) was mixed with GMAC (60.8 g) using a pestle and mortar, and added to the vibration mill described in the Preparation Example 1. After pulverization treatment for 12 minutes (frequency of 20 Hz, total amplitude of 8 mm, and temperature of from 10 to 40° C.), powdery mixture of cellulose and GMAC was obtained.

Further, 48% aqueous solution of sodium hydroxide (29.8 g) was added to the vibration mill, and a pulverization treatment under the same pulverization condition using the vibration mill was performed for 60 minutes to give cationized cellulose.

(3) Step for Obtaining Hydroxypropylation:

A kneader to which the cationized cellulose (190 g) obtained from above step was added was heated to 70° C., added dropwise with propylene oxide (18.0 g) under stirring, and the reaction was allowed to occur for 6 hours until the reflux stops by consumption of propylene oxide.

(4) Cationizing Reaction (2):

The mixture after the reaction was transferred from the kneader to a mortar, GMAC (87.5 g, equivalent to 0.8 mol per mol of AGU) was added, and stirred for 10 minutes at room temperature. After that, it was brought back to the kneader, and the reaction was performed under stirring for 5 hours at 50° C. to give crude C-HPC powder with pale brown color (295 g).

To the obtained crude C-HPC powder, GMAC (87.5 g) was again added, and then the procedure to the reaction at 50° C. was similarly carried out. The above procedures were repeated seven times in total (total amount of the added propylene oxide was 612.5 g; equivalent to 5.3 mol per mol of AGU). The reaction product (10.0 g) was collected and neutralized with lactic acid to obtain pale brown solid. For the purpose of obtaining substitution degrees of the propyleneoxy group and cationized ethyleneoxy group, the product was purified by using a dialysis membrane (molecular weight cut off: 1000) and the aqueous solution was subjected to freeze-drying to give purified C-HPC (5).

Substitution degrees of the cationized ethyleneoxy group and propyleneoxy group in the obtained purified C-HPC (5) were found to be 2.36 and 0.2, respectively. Further, the average polymerization degree was found to be 432.

Preparation Example 6

Preparation of C-HPC (6)

(1) Chipping Step:

Sheet-shape wood pulp (Biofloc HV+ manufactured by Tembec, average polymerization degree of 1604, α-cellulose content of 93.0%, crystallinity of 74%, and moisture content of 7.0%) was formed in a chip shape (from 3 to 5 mm square) after treatment using a sheet pelletizer ("SGG-220", manufactured by HORAI Co, Ltd.).

The obtained chip-shape pulp was added to a vacuum dryer (product name: VO-402, manufactured by Advantec Toyo Kaisha, Ltd.) and dried for 2 hours at 105° C., 20 kPa under nitrogen stream to give dry chip-shape pulp (average polymerization degree: 1604, α-cellulose content: 99.2%, crystallinity: 74%, and moisture content: 0.8%).

(2) Step for Obtaining Alkali Cellulose (Step 1)

The obtained dry chip-shape pulp (920 g) was supplied to a vibration rod mill ("FV-10" manufactured by CHUO KAKOHKI Co., Ltd.: total vessel volume of 35 L, 63 rods were used in which each rod has diameter of 30 mm). After performing pulverizing treatment for 10 minutes (frequency of 20 Hz, amplitude of 8 mm, and temperature of from 10 to 40° C.), powdery pulp with lowered crystallinity (920 g, average polymerization degree: 1198, crystallinity: 14%, moisture content: 1.0%) was obtained as cellulose-containing raw material (I).

(Step 2)

Powdery pulp (460 g) obtained from above (step 1) as cellulose-containing raw material (I) was supplied to a mixer ("Redige mixer" with volume of 5 L, manufactured by MATSUBO Corporation), and while being stirred with main wing at 250 rpm and chopper wing at 2500 rpm, 42.5% aqueous solution of sodium hydroxide (266.8 g (equivalent to 1.0 mol per mol of AGU of cellulose in the cellulose-containing raw material (I) (hereinafter, also referred to as "raw material (II) cellulose), and 33% of water per raw material (II) cellulose)) was added for 1.5 minutes by spraying. After the spraying, the internal temperature was increased to 50° C. and aged under stirring for 3 hours to obtain an alkali cellulose mixture.

(3) Reaction Step for Obtaining Hydroxypropylation:

The alkali cellulose mixture (720.5 g) obtained from above (2) was added to the Redige mixer and the temperature was increased to 50° C. while being stirred with main wing at 50 rpm and chopper wing at 400 rpm. After that, propylene oxide (571.4 g, equivalent to 3.5 mol per mol of AGU of the alkali cellulose) was added dropwise thereto for 3.5 hours. Once the dropwise addition was completed, it was aged for 2 hours at 50° C.

(4) Cationizing Reaction, Neutralization Step:

The reaction mixture obtained from the hydroxypropylation process was aged by keeping it for 6 months in a refrigerator (5° C.), and a sugar chain was slowly cut off. The reaction mixture after low temperature aging (5.0 g) and 65% aqueous solution of 3-chloro-2-hydroxypropyltrimethyl ammonium chloride (manufactured by Yokkaichi Chemical Co., Ltd.) (1.38 g, equivalent to 0.45 mol per mol of AGU which constitutes the cellulose skeleton of the compound containing cellulose skeleton in the reaction mixture that has been obtained by hydroxypropylation) were mixed with each other using a pestle and mortar, and aged by keeping it for 5 hours in a sealed reactor (50° C.) to prepare crude C-HPC. Subsequently, 29% aqueous solution of lactic acid was used for neutralization of the crude C-HPC.

The crude C-HPC powder (2.0 g) was collected. For the purpose of obtaining substitution degrees of the propyleneoxy group and cationized ethyleneoxy group, the neutralization product was purified by using a dialysis membrane (molecular weight cut off: 1000) and the aqueous solution was subjected to freeze-drying to give purified C-HPC (6).

As a result of the analysis of the purified product, substitution degrees of the cationic group and propyleneoxy group were found to be 0.20 and 2.1, respectively. Further, the viscosity average polymerization degree of the obtained C-HPC (6) was found to be 100.

TABLE 1

| | | Average polymerization degree | Substitution degree of cationized EO *1 | Substitution degree of PO *2 |
|---|---|---|---|---|
| Preparation Example 1 | C-HPC(1) | 693 | 0.22 | 1.13 |
| Preparation Example 2 | C-HPC(2) | 693 | 0.18 | 2.0 |
| Preparation Example 3 | C-HPC(3) | 743 | 0.11 | 2.0 |
| Preparation Example 4 | C-HPC(4) | 1300 | 0.10 | 2.9 |
| Preparation Example 5 | C-HPC(5) | 432 | 2.36 | 0.2 |
| Preparation Example 6 | C-HPC(6) | 100 | 0.20 | 2.1 |

*1: Substitution degree of cationized ethyleneoxy group (p)
*2: Substitution degree of propyleneoxy group (q)

Preparation Example 7

Preparation of C-HPC (7)

(1) Chipping Step:

Sheet-shape wood pulp (Biofloc HV10 manufactured by Tembec, average polymerization degree of 1508, crystallinity of 74%, and moisture content of 7.6%) was formed in a chip shape (from 3 to 5 mm square) after treatment using a sheet pelletizer ("SGG-220", manufactured by HORAI Co, Ltd.).

(2) Cationizing Reaction Step:

The chip-shape pulp (2100 g) obtained from the above step (1) and an aqueous solution of glycidyl trimethyl ammonium chloride (hereinafter, also referred to as "GMAC", manufactured by Sakamoto Yakuhin Kogyo Co., Ltd., moisture content of 20%, and purity of 90% or higher) (1170 g, equivalent to 0.52 mol per mol of anhydroglucose unit of cellulose (hereinafter, also referred to as "AGU")) were mixed with each other in a plastic bag and then supplied to a batch type vibration mill ("FV-20" manufactured by CHUG KAKOHKI Co., Ltd.: total vessel volume 69 L, 114 rods made of SUS304, in which each rod has φ of 30 mm, length of 600 mm, and round cross section, and filling ratio of 71%). By performing a pulverization treatment for 12 minutes at frequency of 60 Hz, amplitude of 8 mm, and temperature of from 10 to 40° C., a powdery mixture of cellulose and GMAC was obtained.

Further, 284 g (equivalent to 0.6 mol per mol of AGU) of particulate NaOH was supplied to a vibration mill. The pulverization treatment was performed for 120 minutes under the same condition to give a cationized cellulose.

(3) Reaction Step for Obtaining Hydroxypropylation:

The cationized cellulose (170 g) obtained from the above step (2) was injected to a 1 L kneader equipped with a reflux condenser (PNV-1 type, manufactured by IRIE SHOKAI Co., Ltd.). The temperature was increased to 70° C. and propylene oxide (51 g, equivalent to 2.0 mol per mol of AGU, special grade reagent manufactured by Kanto Chemical Co., Inc.) was added dropwise thereto while stirring and the reaction was performed for 6 hours until the reflux stops by consumption of propylene oxide.

The mixture after the reaction was collected from the kneader to give a crude C-HPC powder with pale brown (220 g). 10.0 g of the crude C-HPC powder was collected and neutralized with lactic acid. For the purpose of obtaining substitution degrees of the propyleneoxy group and cationized ethyleneoxy group, the neutralization product was purified by using a dialysis membrane (molecular weight cut off: 1000) and the aqueous solution was subjected to freeze-drying to give a purified C-HPC (7).

Production conditions for the above step are summarized in Table 2.

From the elemental analysis of the purified C-HPC (7) thus obtained, content of chloride atom was found to be 3.80%. Further, content of hydroxypropoxy group measured in accordance with the "Method for analysis of hydroxypropyl cellulose" described above was 36.5%. The average polymerization degree of the obtained purified C-HPC (7), and substitution degree of the cationized ethyleneoxy group and substitution degree of the propyleneoxy group are described in Tables 2 and 4.

Preparation Example 8

Preparation of C-HPC (8)

(1) Chipping Step:

Sheet-shape wood pulp (Biofloc HV+ manufactured by Tembec, average polymerization degree of 1770, crystallinity of 74%, and moisture content of 7.0%) was formed in a chip shape (from 3 to 5 mm square) after treatment using a sheet pelletizer ("SGG-220", manufactured by HORAI Co, Ltd.).

(2) Cationizing Reaction Step:

The chip-shape pulp (100 g) obtained from the above step (1) and GMAC (58.5 g, equivalent to 0.2 mol per mol of AGU) were mixed with each other using a pestle and mortar and then supplied to a batch type vibration mill ("MB-1" manufactured by CHUO KAKOHKI Co., Ltd.: total vessel volume of 3.5 L, 13 rods made of SUS304, in which each rod has φ of 30 mm, length of 218 mm, and round cross section, and filling ratio of 57%). By performing a pulverization treatment for 12 minutes at frequency of 20 Hz, total amplitude of 8 mm, and temperature of from 30 to 70° C., a powdery mixture of cellulose and GMAC was obtained.

Further, 10.3 g (equivalent to 0.23 mol per mol of AGU) of 48% aqueous solution of sodium hydroxide was added to the obtained powdery mixture, mixed using a pestle and mortar, and then supplied to the batch type vibration mill. The pulverization treatment was performed for 60 minutes under the same condition to give a cationized cellulose.

(3) Hydroxypropylation Reaction Step:

The cationized cellulose (127 g) obtained from the above step (2) was injected to the 1 L kneader equipped with a reflux condenser as used in the Preparation Example 7. The temperature was increased to 70° C. and propylene oxide (45 g, equivalent to 2.8 mol per mol of AGU) was added dropwise thereto while stirring and the reaction was performed for 6 hours until the reflux stops by consumption of propylene oxide. As a result, a crude C-HPC powder with pale brown was obtained (181.0 g).

The crude C-HPC powder was subjected to neutralization, purification, and freeze-drying, in accordance with the Preparation Example 7, to give the purified C-HPC (8). The average polymerization degree of the obtained purified C-HPC (8), and substitution degree of the cationized ethyleneoxy group and substitution degree of the propyleneoxy group are described in Tables 2 and 4.

Preparation Example 9

Preparation of C-HPC (9)

(1) Chipping Step:

Sheet-shape wood pulp (Biofloc HV+ manufactured by Tembec, average polymerization degree of 1604, α-cellulose content of 93.0%, crystallinity of 74%, and moisture content of 7.0%) was formed in a chip shape (from 3 to 5 mm square) after treatment using a sheet pelletizer ("SGG-220", manufactured by HORAI Co, Ltd.).

The obtained chip-shape pulp was added to a vacuum dryer (product name: VO-402, manufactured by Advantec Toyo Kaisha, Ltd.) and dried for 2 hours at 105° C., 20 kPa under nitrogen stream to give dry chip-shape pulp (average polymerization degree: 1604, α-cellulose content: 99.2%, crystallinity: 74%, and moisture content: 0.8%).

(2) Production of Alkali Cellulose (Step 1)

The obtained dry chip-shape pulp (920 g) was supplied to a vibration rod mill ("FV-10" manufactured by CHUG KAKOHKI Co., Ltd.: total vessel volume of 35 L, 63 rods made of SUS304, in which each rod has diameter of 30 mm, length of 510 nm, and round cross section, and filling ratio of 70%). After performing pulverizing treatment for 10 minutes (frequency of 20 Hz, amplitude of 8 mm, and temperature of from 10 to 40° C.), powdery pulp with lowered crystallinity (920 g, average polymerization degree: 1198, crystallinity: 14%, moisture content: 1.0%) was obtained as cellulose-containing raw material (I).

(Step 2)

Powdery pulp (530 g) obtained from above step (1) as cellulose-containing raw material (I) was supplied to a mixer ("Redige mixer" with volume of 5 L, manufactured by MATSUBO Corporation), and while being stirred with main wing at 250 rpm and chopper wing at 2500 rpm, 43% aqueous solution of sodium hydroxide (307 g (equivalent to 1.0 mol per mol of AGU of cellulose in the cellulose-containing raw material (I) (hereinafter, also referred to as "raw material (II) cellulose), and 33.3% of water per raw material (II) cellulose)) was added for 20 sec by spraying. After the spraying, the internal temperature was increased to 50° C., and aged under stirring for 2.5 hours to obtain an alkali cellulose mixture.

(3) Etheration Reaction Step; Reaction Step for Obtaining Hydroxypropylation:

The alkali cellulose mixture (720.4 g) obtained from above step 2 was added to the Redige mixer and the temperature was increased to 50° C. while being stirred with main wing at 50 rpm and chopper wing at 400 rpm. After that, propylene oxide (571.4 g, equivalent to 3.5 mol per mol of AGU of the alkali cellulose mixture) was added dropwise thereto for 3.5 hours. Once the dropwise addition was completed, it was aged for 2 hours at 50° C.

(4) Etherification Reaction Step; Cationizing Reaction Step:

The obtained hydroxypropyl cellulose (226.4 g) was added to a high speed mixer (2 L total volume, manufactured by Fukae Pautec, Co., Ltd.). Under stirring with main wing at 337 rpm (running speed: 3 m/s) and side wing at 1800 rpm, a metallic vessel (500 mL) was installed on top of the mixer via a ball valve, and 3-chloro-2-hydroxypropyltrimethyl ammonium chloride (manufactured by Yokkaichi Chemical Co., Ltd., moisture content of 30% and purity of 70%) (109.1 g) was added to the vessel. The jacket was heated and stirred for 2 hours under temperature control (internal temperature: 50° C.) to give a crude C-HPC.

The crude C-HPC was neutralized with lactic acid. Further, for the purpose of obtaining the substitution degree of the propyleneoxy group, the neutralization product was purified by using a dialysis membrane (molecular weight cut off: 1000) and the aqueous solution was subjected to freeze-drying to give a purified C-HPC (9).

The average polymerization degree of the obtained purified C-HPC (9), and substitution degree of the cationized ethyleneoxy group and substitution degree of the propyleneoxy group are described in Tables 3 and 4.

Preparation Example 10

Preparation of C-HPC (10)

(1) Chipping Step:

Sheet-shape wood pulp (Biofloc HV+ manufactured by Tembec, average polymerization degree of 1604, α-cellulose content of 93.0%, crystallinity of 74%, and moisture content of 7.0%) was formed in a chip shape (from 3 to 5 mm square) after treatment using a sheet pelletizer ("SGG-220", manufactured by HORAI Co, Ltd.).

The obtained chip-shape pulp was added to a vacuum dryer (product name: VO-402, manufactured by Advantec Toyo Kaisha, Ltd.) and dried for 2 hours at 105° C., 20 kPa under nitrogen stream to give dry chip-shape pulp (average polymerization degree: 1604, α-cellulose content: 99.2%, crystallinity: 74%, and moisture content: 0.8%).

(2) Production of Alkali Cellulose (Step 1)

The obtained dry chip-shape pulp (920 g) was supplied to a vibration rod mill ("FV-10" manufactured by CHUG KAKOHKI Co., Ltd.: total vessel volume of 35 L, 63 rods made of SUS304, in which each rod has diameter of 30 mm, length of 510 nm, and round cross section, and filling ratio of 70%). After performing pulverizing treatment for 10 minutes (frequency of 20 Hz, amplitude of 8 mm, and temperature of from 10 to 40° C.), a powdery pulp with lowered crystallinity (920 g, average polymerization degree: 1198, crystallinity: 14%, moisture content: 1.0%) was obtained as a cellulose-containing raw material (I).

(Step 2)

The powdery pulp (4450 g) obtained from above step (1) as cellulose-containing raw material (I) was supplied to a mixer (75 L total volume, "Pro Share mixer" manufactured by Pacific Machinery & Engineering Co., Ltd), and while being stirred with main wing at 3 m/s and chopper wing at 1800 rpm, 43% aqueous solution of sodium hydroxide (2580 g (equivalent to 1.0 mol per mol of AGU of raw material (II) cellulose, and 31% of water per raw material (II) cellulose)) was added for 1.5 minutes by spraying. After the spraying, the internal temperature was increased to 50° C. and aged under stirring for 3 hours to obtain an alkali cellulose mixture.

(3) Etherification Reaction Step; Reaction Step for Obtaining Hydroxypropylation:

The alkali cellulose mixture (7030 g) obtained from above step 2 was stirred in the Pro Share mixer with main wing at 1 m/s and chopper wing at 400 rpm while the temperature was increased to 50° C. After that, propylene oxide (5580 g, equivalent to 3.5 mol per mol of AGU of the alkali cellulose mixture) was added dropwise thereto for 6 hours. Once the dropwise addition was completed, it was aged for 3 hours at 50° C.

(4) Etherification Reaction Step; Cationizing Reaction Step:

The obtained hydroxypropyl cellulose (192.0 g) was added to a high speed mixer (2 L total volume, manufactured by Fukae Pautec, Co., Ltd.). Under stirring with main wing at 337 rpm (running speed: 3 m/s) and side wing at 1800 rpm, a metallic vessel (500 mL) was installed on top of the mixer via a ball valve, and 3-chloro-2-hydroxypropyltrimethyl ammonium chloride (manufactured by Yokkaichi Chemical Co., Ltd., moisture content of 30% and purity of 70%) (95.08 g) was added to the vessel. The jacket was heated and stirred for 2 hours under temperature control (internal temperature: 50° C.) to give a crude C-HPC.

The crude C-HPC was neutralized with lactic acid. Further, for the purpose of obtaining the substitution degree of the propyleneoxy group, the neutralization product was purified by using a dialysis membrane (molecular weight cut off: 1000) and the aqueous solution was subjected to freeze-drying to give a purified C-HPC (10).

The average polymerization degree of the obtained purified C-HPC (10), and substitution degree of the cationized ethyleneoxy group and substitution degree of the propyleneoxy group are described in Tables 3 and 4.

TABLE 2

| | Raw material pulp | | | Cationizing reaction step | | | | | |
|---|---|---|---|---|---|---|---|---|---|
| | Crystallinity (%) | Average polymerization degree | Moisture content (%) | Use amount of pulp (g) | Vibration mill | GMAC Addition amount (g) | Pulverization time (minutes) | 48% NaOH Addition amount (g) | Pulverization time (minutes) |
| Preparation Example 7: C-HPC (7) | 74 | 1508 | 7.6 | 2100 | FV-20 | 1170 | 12 | 284 | 120 |
| Preparation Example 8: C-HPC (8) | 74 | 1770 | 7.0 | 100 | MB-1 | 58.5 | 12 | 10.3 | 60 |

| | Hydroxypropylation reaction step | | | C-HPC | | |
|---|---|---|---|---|---|---|
| | Use amount of cationized cellulose (g) | Addition amount of propylene oxide (g) | Reaction time (hr) | Average polymerization degree | Chlorine content (%) | Content of hydroxypropoxy group (%) |
| Preparation Example 7: C-HPC (7) | 170 | 51 | 6 | 1302 | 3.80 | 36.5 |
| Preparation Example 8: C-HPC (8) | 127 | 45 | 6 | 744 | 4.01 | 28.3 |

TABLE 3

| | Raw material pulp | | | Pulverization step | | | Hydroxypropylation reaction step | | | |
|---|---|---|---|---|---|---|---|---|---|---|
| | Crystallinity (%) | Average polymerization degree | Moisture content (%) | Use amount of chip-shape pulp (g) | Vibration mill | Pulverization time (minutes) | Use amount of powdery pulp (g) | 43% NaOH aq. Addition amount (g) | Addition amount of propylene oxide (g) | Reaction time (hr) |
| Preparation Example 9: C-HPC(9) | 74 | 1604 | 7.0 | 920 | FV-10 | 10 | 530 | 307 | 571.4 | 7 |
| Preparation Example 10: C-HPC(10) | 74 | 1604 | 7.0 | 920 | FV-10 | 10 | 4450 | 2580 | 5580 | 9 |

| | Cationizing reaction step | | | C-HPC | | |
|---|---|---|---|---|---|---|
| | Use amount of HPC (g) | HAC Addition amount (g) | Reaction time (hr) | Average polymerization degree | Chlorine content (%) | Content of hydroxypropoxy group (g) |
| Preparation Example 9: C-HPC(9) | 226 | 109 | 2 | 696 | 2.98 | 32.8 |
| Preparation Example 10: C-HPC(10) | 192 | 95 | 2 | 588 | 3.71 | 35.6 |

TABLE 4

| | | Average polymerization degree | Substitution degree of cationized EO *1 | Substitution degree of PO *2 |
|---|---|---|---|---|
| Preparation Example 7 | C-HPC(7) | 1302 | 0.3 | 1.3 |
| Preparation Example 8 | C-HPC(8) | 744 | 0.3 | 1.0 |
| Preparation Example 9 | C-HPC(9) | 696 | 0.3 | 1.7 |
| Preparation Example 10 | C-HPC(10) | 588 | 0.3 | 2.0 |

*1 Substitution degree of cationized ethyleneoxy group
*2 Substitution degree of propyleneoxy group Examples 1 to 12 and Comparative Examples 1 and 2

The skin cleansing composition having the composition listed in Table 5 was produced in accordance with the following method. Quickness of lathering, foam quality, foam volume during washing, foam volume during rinsing, strength of stop feeling during rinsing, skin feel immediately after towel drying, and skin feel after drying were evaluated for the obtained skin cleansing composition. The results are also listed in Table 5.

(Preparation Method)

After dispersing powdery C-HPC in water at 20° C., each component was mixed in order, fully stirred, and dissolved to give a skin cleansing composition.

(Evaluation Method)

(1) Quickness of Lathering:

Each skin cleansing composition (1 g) was picked up by hands, diluted with tap water at 30° C. to approximately five times. After briefly bubbling for 5 seconds with both hands, quickness of lathering was evaluated. The evaluation was made based on the following criteria, and expressed as an average value given by five professional panelists.

5; It was felt that the lathering (property) was very fast.
4; It was felt that the lathering (property) was fast.
3; It was felt that the lathering (property) was moderate.
2; It was felt that the lathering (property) was slightly slow.
1; It was felt that the lathering (property) was slow.

(2) Foam Quality (Creamy):

Each skin cleansing composition (1 g) was picked up by hands, diluted with tap water at 30° C. to approximately five times. After briefly bubbling for 20 seconds with both hands, foam quality (creamy) was evaluated. The evaluation was made based on the following criteria, and expressed as an average value given by five professional panelists.

5; It was felt that the texture was fine and very creamy, and the foam quality was found to be good.
4; It was felt to be creamy, and the foam quality was found to be good.
3; It was felt that foam quality was slightly creamy.
2; It was felt that foam quality was slightly light and grainy.
1; It was felt that foam quality was light and grainy.

(3) Foam Volume During Washing:

Each skin cleansing composition was diluted with hard water (hardness: 4) to 50-fold (equivalent to the condition upon washing the body) to provide a sample aqueous solution. The sample aqueous solution (7.5 mL) was placed in a graduated 50 mL glass cylinder (23 mm×180 mm) equipped with a stopper cock, and a cover was put thereon. Using a shaker (manufactured by Iwaki Sangyo K.K.; Model No.: "UNIVERSAL SHAKER V-SX"), the cylinder was shaken for 30 seconds at a rate of 300 strokes/min, and immediately after the completion of the shaking, the volume of foam was read (cm).

(4) Foam Volume During Rinsing (Easiness of Foam Disappearance During Rinsing):

Each skin cleansing composition was diluted with hard water (hardness: 4) to 400-fold with assumption of foam disappearance after rinsing to provide a sample aqueous solution. The sample aqueous solution (7.5 mL) was placed in a graduated 50 mL glass cylinder (35 mm×78 mm) equipped with a stopper cock, and a cover was put thereon. Using a shaker (manufactured by Iwaki Sangyo K.K.; Model No.: "UNIVERSAL SHAKER V-SX"), the cylinder was shaken for 30 seconds at a rate of 300 strokes/min, and immediately after the completion of the shaking, the volume of foam was read (cm).

(5) Strength of Stop Feeling Upon Completion of Rinsing

Each skin cleansing composition (1 g) was picked up by hands, diluted with tap water at 30° C. to approximately five times. After briefly bubbling for 20 seconds with both hands, the foams were evenly spread on one entire arm (that is, from elbow to end of wrist), and then rinsed with tap water. At that time, both forearms were rinsed with rubbing, and based on the strength of stop feeling upon completion of the rinsing, rinsing performance was evaluated. The evaluation was made based on the following criteria, and expressed as an average value given by five professional panelists.

5; It was felt that the stop feeling was very strong upon finishing rinsing.
4; It was felt that the stop feeling was strong upon finishing rinsing.
3; It was felt that the stop feeling was mild upon finishing rinsing.
2; It was felt that the stop feeling was slightly weak upon finishing rinsing.
1; It was felt that the stop feeling was weak upon finishing rinsing.

(6) Skin Feel Immediately after Towel Drying

Ten professional panelists washed their whole bodies once a day with each skin cleansing composition. The same procedure was repeated consecutively for three days. Immediately after towel drying, moist feel like the hands adsorbing onto the skin was evaluated for the inside of an arm using palm of the other hand. The results were expressed as the number of people who replied that they strongly felt the feel like the hands adsorbing onto the skin.

(7) Skin Feel after Drying:

Ten professional panelists washed their whole bodies once a day with each skin cleansing composition. The same procedure was repeated consecutively for three days. Ten minutes after towel drying, the evaluation to the skin was expressed by the number of people who replied that they strongly felt smoothness of the skin with moist feel.

TABLE 5

| | Component (% by weight) | Example 1 | 2 | 3 | 4 | 5 | 6 | 7 |
|---|---|---|---|---|---|---|---|---|
| (A) | Sodium polyoxyethylene (1) lauryl ether sulfate *1 | 10.0 | 10.0 | 10.0 | 10.0 | 10.0 | 10.0 | 10.0 |
| | Potassium laurate | | | | | | | |
| (B) | ethylhexyl glyceryl ether *2 | 0.5 | 0.5 | 0.5 | 0.5 | 0.5 | 0.5 | 0.5 |
| (C) | C-HPC (1) (cationizing degree: 0.22, PO substitution degree: 1.13) | 0.5 | 0.5 | 0.5 | 0.5 | 0.5 | 0.5 | 0.5 |
| (D) | water | Balance | Balance | Balance | Balance | Balance | Balance | Balance |
| (E1) | 3-methyl-1-vinyl-1H-diimidazolium chloride•1-vinyl-2-pyrrolidone copolymer *3 | | 0.3 | | | | 0.3 | 0.3 |
| (E2) | acrylic acid•alkyl methacrylate copolymer *4 | | | 0.3 | | | | |
| (E3) | polyethylene glycol (molecular weight 2500000) *5 | | | | 0.3 | | | |
| (E4) | Dimethyl diallyl ammonium chloride•acrylic acid•acrylamide (45:17:38) copolymer *6 | | | | | 0.3 | | |
| (F) | alkyl (C10-16) polyglucoside *7 | | | | | | 3.2 | 3.2 |
| (G) | lauric acid amide propylbetaine *8 | | | | | | | 3.0 |
| | hydroxyethyl cellulose hydroxypropyl trimethyl ammonium chloride ether *9 | | | | | | | |
| | Dimethyl diallyl ammonium chloride•acrylamide (50:50) copolymer *10 | | | | | | | |
| | Total | 100 | 100 | 100 | 100 | 100 | 100 | 100 |
| | (C)/(B)mass ratio | 1.00 | 1.00 | 1.00 | 1.00 | 1.00 | 1.00 | 1.00 |
| | (E1)/(C) or (E2)/(C)mass ratio | | 0.60 | 0.60 | | | 0.60 | 0.60 |
| | quickness of lathering | 4.4 | 4.4 | 4.4 | 4.4 | 4.4 | 4.4 | 4.8 |

TABLE 5-continued

| | 4.2 | 4.6 | 4.6 | 4.4 | 4.4 | 4.6 | 4.6 |
|---|---|---|---|---|---|---|---|
| foam quality (creamy) | 4.2 | 4.6 | 4.6 | 4.4 | 4.4 | 4.6 | 4.6 |
| foam volume during washing (cm) | 5 | 5 | 5 | 5 | 4.9 | 5.2 | 5.2 |
| foam volume during rinsing (cm) | 2.5 | 2.7 | 2.8 | 2.8 | 2.7 | 3.9 | 4.3 |
| strength of stop feeling upon finishing rinsing | 4.2 | 4.6 | 4.4 | 4.2 | 4.2 | 4.6 | 4.6 |
| skin feel immediately after towel drying: feel like the hands adsorbing onto the hand (number of people) | 8 | 8 | 8 | 8 | 7 | 9 | 9 |
| skin feel after drying: smoothness with moist feel (number of people) | 8 | 8 | 8 | 9 | 8 | 8 | 8 |

| | Component (% by weight) | Example 8 | Example 9 | Example 10 | Example 11 | Example 12 | Comparative example 1 | Comparative example 2 |
|---|---|---|---|---|---|---|---|---|
| (A) | Sodium polyoxyethylene (1) lauryl ether sulfate *1 | 10.0 | 10.0 | 10.0 | 10.0 | 10.0 | 10.0 | 10.0 |
| | Potassium laurate | | | | | | | |
| (B) | ethylhexyl glyceryl ether *2 | 0.3 | 0.4 | 0.8 | 1.2 | 2.0 | | 0.5 |
| (C) | C-HPC (1) (cationizing degree: 0.22, PO substitution degree: 1.13) | 1.8 | 1.4 | 0.5 | 0.5 | 0.3 | | |
| (D) | water | Balance | Balance | Balance | Balance | Balance | Balance | Balance |
| (E1) | 3-methyl-1-vinyl-1H-diimidazolium chloride•1-vinyl-2-pyrrolidone copolymer *3 | | | | | | | |
| (E2) | acrylic acid•alkyl methacrylate copolymer *4 | | | | | | | |
| (E3) | polyethylene glycol (molecular weight 2500000) *5 | | | | | | | |
| (E4) | Dimethyl diallyl ammonium chloride•acrylic acid•acrylamide (45:17:38) copolymer *6 | | | | | | | |
| (F) | alkyl (C10-16) polyglucoside *7 | | | | | | | |
| (G) | lauric acid amide propylbetaine *8 | | | | | | | |
| | hydroxyethyl cellulose hydroxypropyl trimethyl ammonium chloride ether *9 | | | | | | 0.3 | 0.5 |
| | Dimethyl diallyl ammonium chloride•acrylamide (50:50) copolymer *10 | | | | | | 0.2 | |
| Total | | 100 | 100 | 100 | 100 | 100 | 100 | 100 |
| (C)/(B) mass ratio | | 6.00 | 3.50 | 0.63 | 0.42 | 0.15 | | |
| (E1)/(C) or (E2)/(C) mass ratio | | | | | | | | |
| quickness of lathering | | 4 | 4.6 | 4.4 | 4.4 | 4 | 3 | 4.4 |
| foam quality (creamy) | | 4 | 4.2 | 4.2 | 4.2 | 4.2 | 3.2 | 3.4 |
| foam volume during washing (cm) | | 4.8 | 6 | 5 | 4.5 | 4.7 | 6.3 | 5.3 |
| foam volume during rinsing (cm) | | 3.1 | 2.8 | 2.5 | 2.6 | 3.2 | 5.2 | 5.2 |
| strength of stop feeling upon finishing rinsing | | 4 | 4.2 | 4.2 | 4.2 | 4 | 3.4 | 2.2 |
| skin feel immediately after towel drying: feel like the hands adsorbing onto the hand (number of people) | | 7 | 8 | 8 | 8 | 7 | 2 | 3 |
| skin feel after drying: smoothness with moist feel (number of people) | | 7 | 8 | 8 | 8 | 7 | 2 | 4 |

*1: manufactured by Kao Corporation, effective component of EMAL 170J
*2: manufactured by Kao Corporation, effective component of BENETOL GE-EH
*3: manufactured by BASF SE, effective component of Luviquat FC550 (cation charge density: 3.3 meq/g)
*4: manufactured by Lubrizol Advanced Materials, effective component of CARBOPOL ETD2020
*5: manufactured by Meisei Chemical Works, Ltd., effective component of ALKOX E-100
*6: manufactured by Ondeo Nalco Company, effective component of MERQUAT PLUS 3331
*7: manufactured by Kao Corporation, effective component of AG-124
*8: manufactured by Kao Corporation, effective component of AMPHITOL 20AB
*9: manufactured by Dow Chemical Company, effective component of UCARE POLYMER LR400 (cation charge density 1 meg/g)
*10: manufactured by Ondeo Nalco Company, effective component of MERQUAT 550 (cation charge density: 3.1 meg/g)

Examples 13 to 21

The skin cleansing composition having the composition listed in Table 6 was produced in the same manner as Examples 1 to 12.

The obtained skin cleansing compositions were found to have quick lathering, foam quality with fine texture, very creamy, excellent lathering property during washing, excellent cleansing feel during use, ease of washing-off with no slimy feel, and after drying, moist feel and smoothness.

TABLE 6

|   | Component (% by weight) | Example 13 | 14 | 15 | 16 | 17 | 18 | 19 | 20 | 21 |
|---|---|---|---|---|---|---|---|---|---|---|
| (A) | Sodium polyoxyethylene (1) lauryl ether sulfate *1 | 5.00 | 5.00 | 4.00 |  | 4.00 | 15.00 | 3.00 | 10.00 | 4.00 |
|  | Sodium polyoxyethylene (2.6) lauryl ether carboxylate *2 |  | 1.00 | 2.00 | 5.00 |  | 1.00 |  |  |  |
|  | Sodium polyoxyethylene (4.5) lauryl ether carboxylate *3 |  | 1.00 | 2.00 | 5.00 | 5.00 | 2.00 |  |  |  |
|  | Potassium laurate |  |  |  | 3.00 | 5.00 |  |  | 3.00 | 1.00 |
|  | Potassium myristate |  |  |  | 9.00 | 5.00 |  |  | 4.00 | 2.00 |
|  | Potassium palmitic acid |  |  |  | 12.00 | 1.00 |  |  | 3.00 |  |
|  | Potassium stearate |  |  |  | 6.00 |  |  |  |  |  |
|  | Sodium cocoylglutamate *4 |  |  | 7.00 |  |  |  |  |  |  |
| (B) | ethylhexyl glyceryl ether *5 | 0.20 | 0.30 | 0.20 | 0.02 | 5.00 | 1.50 | 0.10 | 1.00 | 0.40 |
| (C) | C-HPC (1) (cationizing degree: 0.22, PO substitution degree: 1.13) | 0.30 | 0.30 | 0.10 | 0.01 | 0.50 |  | 0.30 | 2.00 | 0.20 |
|  | C-HPC (2) (cationizing degree: 0.18, PO substitution degree: 2.0) |  | 0.30 |  | 0.01 |  | 0.80 |  | 2.00 |  |
|  | C-HPC (3) (cationizing degree: 0.11, PO substitution degree: 2.0) |  |  | 0.10 |  |  | 0.20 |  | 2.00 |  |
|  | C-HPC (4) (cationizing degree: 0.1, PO substitution degree: 2.9) |  | 0.30 |  |  | 1.00 |  |  | 2.00 |  |
|  | C-HPC (5) (cationizing degree: 2.36, PO substitution degree: 0.2) |  |  |  |  |  | 0.50 | 0.10 | 2.00 |  |
|  | C-HPC (6) (cationizing degree: 0.2, PO substitution degree: 2.1) |  |  |  |  |  |  |  |  | 0.20 |
| (D) | water | Balance | Balance | Balance | Balance | Balance | Balance | Balance | Balance | Balance |
| (E1) | 3-methyl-1-vinyl-1H-imidazolium chloride•1-vinyl-2-pyrrolidone copolymer *6 |  |  | 0.20 |  |  | 0.50 |  | 0.50 | 0.40 |
| (E1) | Dimethyl diallyl ammonium chloride•acrylamide (50:50) copolymer *7 |  | 0.10 |  | 0.10 | 0.50 | 0.30 |  | 0.50 |  |
| (E2) | acrylic acid•alkyl methacrylate copolymer *8 | 0.03 |  | 0.80 | 0.10 | 1.00 | 0.10 | 0.01 | 2.00 | 0.40 |
| (E3) | polyethylene glycol *9 |  |  |  |  | 0.01 | 0.01 |  | 0.10 |  |
|  | hydroxypropyl guar gum *10 |  |  | 0.05 | 0.05 |  | 0.01 |  |  |  |
|  | hydroxypropylmethyl cellulose *11 |  |  | 0.05 | 0.05 |  |  |  | 0.50 |  |
| (E4) | Dimethyl diallyl ammonium chloride•acrylic acid•acrylamide (45:17:38) copolymer *12 |  |  | 0.30 |  | 0.50 | 0.05 |  | 0.40 |  |
| (F) | alkyl (C10-16) polyglucoside *13 | 1.00 |  | 0.30 |  |  | 0.10 | 0.30 | 5.00 | 2.00 |
|  | alkyl (C9-11) glucoside *14 | 1.00 |  |  | 3.00 | 2.00 |  |  |  | 1.00 |
|  | polyoxyethylene (16) lauryl ether *15 |  |  | 0.05 | 0.20 | 3.00 | 2.00 | 0.10 | 0.20 | 5.00 |
| (G) | lauric acid amide propylbetaine *16 | 1.00 | 1.00 | 0.20 |  | 3.00 |  | 0.10 | 5.00 |  |
|  | cocoamide propylbetaine *17 |  | 1.00 |  | 0.05 |  | 1.00 |  | 5.00 | 0.50 |
|  | laurylhydroxy sulfobetaine *18 | 1.00 | 1.00 | 0.30 | 0.05 | 3.00 |  |  |  |  |
|  | propylene glycol |  | 3.00 |  |  | 5.00 | 5.00 | 1.00 | 3.00 |  |
|  | dipropylene glycol | 1.00 |  |  | 2.00 |  |  | 2.00 | 3.00 |  |
|  | glycerin |  |  | 1.00 |  |  | 2.00 |  |  |  |
|  | sorbitol |  |  | 4.00 | 8.00 | 15.00 |  | 5.00 |  |  |
|  | pH adjuster | q.s. | q.s. | q.s. | q.s. | q.s. | q.s. | q.s. | q.s. | q.s. |
| total |  | 100 | 100 | 100 | 100 | 100 | 100 | 100 | 100 | 100 |
| (C)/(B) |  | 1.5 | 3.0 | 1.0 | 1.0 | 0.4 | 0.7 | 4.0 | 10.0 | 1.0 |
| (E1)/(C) |  | 0.00 | 0.11 | 1.0 | 5.0 | 0.8 | 0.9 | 0.0 | 0.10 | 2.00 |
| (E2)/(C) |  | 0.10 | 0.00 | 4.0 | 5.0 | 0.5 | 0.1 | 0.03 | 0.20 | 2.00 |
| pH (20 times dilution) |  | 7.0 | 5.9 | 6.8 | 9.1 | 9.0 | 5.8 | 7.1 | 9.2 | 9.0 |

*1: manufactured by Kao Corporation, effective component of EMAL 170J
*2: manufactured by Kao Corporation, effective component of AKYPO 26
*3: manufactured by Kao Corporation, effective component of KAOAKYPO RLM-45NV
*4: manufactured by Ajinomoto Co., Inc., effective component of AMILITE GCK-11
*5: manufactured by Kao Corporation, effective component of BENETOL GE-EH
*6: manufactured by BASF SE, effective component of Luviquat FC550 (cation charge density: 3.3 meg/g)
*7: manufactured by Ondeo Nalco Company, effective component of MERQUAT 550 (cation charge density: 3.1 meg/g)
*8: manufactured by Lubrizol Advanced Materials, effective component of CARBOPOL ETD2020
*9: manufactured by Meisei Chemical Works, Ltd., effective component of ALKOX E-100
*10: manufactured by Rhodia, effective component of JAGUAR HP-105
*11: manufactured by Shin-Etsu Chemical Co., Ltd., effective component of METOLOSE 60SH-10000
*12: manufactured by Ondeo Nalco Company, effective component of MERQUAT PLUS 3331
*13: manufactured by Kao Corporation, effective component of AG-124
*14: manufactured by Kao Corporation, effective component of AG-10LK
*15: manufactured by Kao Corporation, effective component of EMULGEN 116
*16: manufactured by Kao Corporation, effective component of AMPHITOL 20AB
*17: manufactured by Kao Corporation, effective component of AMPHITOL 55AB
*18: manufactured by Kao Corporation, effective component of AMPHITOL 20HD Examples 22 to 31 and Comparative Examples 3 to 6

The aqueous hair cleansing agent having the composition listed in Table 7 was produced and then evaluated in terms of quickness of lathering, richness of foam volume, lightness of foam quality, ease of movement of finger during hair washing, no slimy feel during rinsing, favorable foam dissipation property during rinsing, and no residual feel after rinsing. The results are also listed in Table 7. pH indicates the value measured at 25° C. after diluted with water to 20 times by weight.

(Evaluation Method)

Hair tress (10 g, length: 25 cm, average diameter: 80 μm, and width: 5.5 cm) (Japanese woman's damaged hair after straight permanent (one time) and bleach (two times)) was treated as follows by five panelists, who subsequently performed a sensory evaluation.

(1) Quickness of Lathering:

The hair tress was briefly rinsed with hot water at 40° C., excess moisture was removed, and sufficiently bubbled for about 30 seconds by using 0.5 g of an aqueous hair cleansing agent. At that time, quickness of lathering was determined by sensory evaluation in accordance with the following five-grade evaluation. The evaluation was made by five people, and the integrated value thereof was obtained.
5: lathering was quick.
4: lathering was slightly quick.
3: lathering was felt to be moderate.
2: lathering was slightly slow.
1: lathering was slow.

(2) Richness of Foam Volume:

The hair tress was briefly rinsed with hot water at 40° C., excess moisture was removed, and then sufficiently bubbled for about 30 seconds by using 0.5 g of an aqueous hair cleansing agent. At that time, richness of hair volume was determined by sensory evaluation in accordance with the following five-grade evaluation. The evaluation thereof was made by five people, and the integrated value was obtained.
5: foam volume was large.
4: foam volume was slightly large.
3: foam volume was felt to be moderate.
2: foam volume was slightly small.
1: foam volume was small.

(3) Lightness of Foam Texture:

The hair tress was briefly rinsed with hot water at 40° C., excess moisture was removed, and sufficiently bubbled for about 30 seconds by using 0.5 g of an aqueous hair cleansing agent. At that time, lightness of foam texture was determined by sensory evaluation in accordance with the following five-grade evaluation. The evaluation was made by five people, and the integrated value thereof was obtained.
5: light foam quality.
4: slightly light foam quality.
3: moderate foam quality.
2: slightly heavy foam quality.
1: heavy foam quality.

(4) Ease of Movement of Finger During Hair Washing

The hair tress was briefly rinsed with hot water at 40° C., excess moisture was removed, and sufficiently bubbled for about 30 seconds by using 0.5 g of an aqueous hair cleansing agent. At that time, ease of movement of finger during hair washing was determined by sensory evaluation in accordance with the following five-grade evaluation. The evaluation was made by five people, and the integrated thereof value was obtained.
5: it was easy to move fingers.
4: it was relatively easy to move fingers.
3: it was not difficult to move fingers.
2: it was slightly difficult to move fingers.
1: it was difficult to move fingers.

(5) No slimy feel during rinsing:

The hair tress was briefly rinsed with hot water at 40° C., excess moisture was removed, and sufficiently bubbled for about 30 seconds by using 0.5 g of an aqueous hair cleansing agent. After that, the slimy feel was determined by sensory evaluation in accordance with the following five-grade evaluation while rinsing the hair tress having foams with hot water at 40° C. at flow rate of 2 L/min. The evaluation was made by five people, and the integrated value thereof was obtained.
5: there was no slimy feel.
4: there was almost no slimy feel.
3: there was normal slimy feel.
2: there was some slimy feel.
1: there was definitely slimy feel.

(6) Favorable Foam Dissipation Property During Rinsing:

The hair tress was briefly rinsed with hot water at 40° C., excess moisture was removed, and sufficiently bubbled for about 30 seconds by using 0.5 g of an aqueous hair cleansing agent. After that, foam dissipation property during rinsing was determined by sensory evaluation in accordance with the following five-grade evaluation while rinsing the hair tress having foams attached thereto with hot water at 40° C. at flow rate of 2 L/min. The evaluation was made by five people, and the integrated value thereof was obtained.
5: favorable foam dissipation property.
4: slightly favorable foam dissipation property.
3: moderate foam dissipation property.
2: slightly unfavorable foam dissipation property.
1: unfavorable foam dissipation property.

(7) No Residual Feel after Rinsing:

The hair tress was briefly rinsed with hot water at 40° C., excess moisture was removed, and sufficiently bubbled for about 30 seconds by using 0.5 g of an aqueous hair cleansing agent. After that, the residual feel was determined by sensory evaluation in accordance with the following five-grade evaluation while rinsing the hair tress having foams attached thereto with hot water at 40° C. at flow rate of 2 L/min. The evaluation was made by five people, and the integrated value thereof was obtained.
5: there was no residual feel.
4: there was almost no residual feel.
3: there was normal residual feel.
2: there was some residual feel.
1: there was definitely residual feel.

TABLE 7

| | Component (% by weight) | Example 22 | 23 | 24 | 25 | 26 | 27 | 28 |
|---|---|---|---|---|---|---|---|---|
| (A) | ammonium lauryl ether (1) sulfate *1 | 12.5 | 10.0 | 12.5 | 12.5 | 12.5 | 12.5 | 12.5 |
| | sodium lauryl ether (2) sulfate *2 | — | 2.5 | — | — | — | — | — |
| (B) | C-HPC(7) *3 | 0.3 | 0.3 | — | 0.3 | 0.1 | 0.5 | 0.3 |
| | C-HPC(8) *4 | — | — | 0.3 | — | — | — | — |
| | C-HPC(9) *5 | — | — | — | — | — | — | — |
| | C-HPC(10) *6 | — | — | — | — | — | — | — |
| (C) | 2-ethylhexy glyceryl ether *7 | 1.64 | 1.64 | 1.64 | — | 1.64 | 1.64 | 0.8 |
| | isodecyl glyceryl ether *8 | — | — | — | 1.64 | — | — | — |

TABLE 7-continued

| | | | | | | | | |
|---|---|---|---|---|---|---|---|---|
| other components | HPC *9 | — | — | — | — | — | — | — |
| | C-HEC *10 | — | — | — | — | — | — | — |
| | lauryl hydroxy sultaine | 1.7 | 1.7 | 1.7 | 1.7 | 1.7 | 1.7 | 1.7 |
| | lauric acid | 0.4 | 0.4 | 0.4 | 0.4 | 0.4 | 0.4 | 0.4 |
| | malic acid | 0.55 | 0.55 | 0.55 | 0.55 | 0.55 | 0.55 | 0.55 |
| | lactic acid | 0.2 | 0.2 | 0.2 | 0.2 | 0.2 | 0.2 | 0.2 |
| | ethylene glycol distearyl | 1.6 | 1.6 | 1.6 | 1.6 | 1.6 | 1.6 | 1.6 |
| | cationized guar gum *11 | 0.2 | 0.2 | 0.2 | 0.2 | 0.2 | 0.2 | 0.2 |
| | dimethyl polysiloxane emulsion *12 | 0.3 | 0.3 | 0.3 | 0.3 | 0.3 | 0.3 | 0.3 |
| | sodium benzoate | 0.1 | 0.1 | 0.1 | 0.1 | 0.1 | 0.1 | 0.1 |
| | sodium chloride | 0.4 | 0.4 | 0.4 | 0.4 | 0.4 | 0.4 | 0.4 |
| | potassium hydroxide (adjust pH to 3.7) | q.s. | q.s. | q.s. | q.s. | q.s. | q.s. | q.s. |
| | purified water | balance | balance | balance | balance | balance | balance | balance |
| total | | 100 | 100 | 100 | 100 | 100 | 100 | 100 |
| (B)/(A) | | 0.024 | 0.024 | 0.024 | 0.024 | 0.008 | 0.04 | 0.024 |
| (B)/(C) | | 0.183 | 0.183 | 0.183 | 0.183 | 0.061 | 0.305 | 0.375 |
| pH | | 3.7 | 3.7 | 3.7 | 3.7 | 3.7 | 3.7 | 3.7 |
| evaluation | quickness of lathering | 23 | 24 | 22 | 22 | 22 | 24 | 20 |
| | richness of foam volume | 25 | 25 | 23 | 24 | 21 | 25 | 21 |
| | lightness of foam quality | 24 | kai | 24 | 24 | 23 | 25 | 23 |
| | ease of movement of finger during bubbling | 24 | 22 | 23 | 23 | 22 | 24 | 24 |
| | no slimy feel during rinsing | 24 | 22 | 24 | 24 | 23 | 24 | 24 |
| | favorable dissipation property during rinsing | 22 | 23 | 23 | 22 | 21 | 23 | 22 |
| | no residual feel after rinsing | 23 | 23 | 23 | 24 | 23 | 23 | 22 |

| | | Example | | | Comparative example | | | |
|---|---|---|---|---|---|---|---|---|
| | Component (% by weight) | 29 | 30 | 31 | 3 | 4 | 5 | 6 |
| (A) | ammonium lauryl ether (1) sulfate *1 | 12.5 | 12.5 | 12.5 | 12.5 | 12.5 | 12.5 | 12.5 |
| | sodium lauryl ether (2) sulfate *2 | — | — | — | — | — | — | — |
| (B) | C-HPC(7) *3 | 0.3 | — | — | — | — | — | 0.3 |
| | C-HPC(8) *4 | — | — | — | — | — | — | — |
| | C-HPC(9) *5 | — | 0.3 | — | — | — | — | — |
| | C-HPC(10) *6 | — | — | 0.3 | — | — | — | — |
| (C) | 2-ethylhexy glyceryl ether *7 | 3.2 | 1.64 | 1.64 | 1.64 | 1.64 | 1.64 | — |
| | isodecyl glyceryl ether *8 | — | — | — | — | — | — | — |
| other components | HPC *9 | — | — | — | 0.3 | — | — | — |
| | C-HEC *10 | — | — | — | — | 0.3 | — | — |
| | lauryl hydroxy sultaine | 1.7 | 1.7 | 1.7 | 1.7 | 1.7 | 1.7 | 1.7 |
| | lauric acid | 0.4 | 0.4 | 0.4 | 0.4 | 0.4 | 0.4 | 0.4 |
| | malic acid | 0.55 | 0.55 | 0.55 | 0.55 | 0.55 | 0.55 | 0.55 |
| | lactic acid | 0.2 | 0.2 | 0.2 | 0.2 | 0.2 | 0.2 | 0.2 |
| | ethylene glycol distearyl | 1.6 | 1.6 | 1.6 | 1.6 | 1.6 | 1.6 | 1.6 |
| | cationized guar gum *11 | 0.2 | 0.2 | 0.2 | 0.2 | 0.2 | 0.2 | 0.2 |
| | dimethyl polysiloxane emulsion *12 | 0.3 | 0.3 | 0.3 | 0.3 | 0.3 | 0.3 | 0.3 |
| | sodium benzoate | 0.1 | 0.1 | 0.1 | 0.1 | 0.1 | 0.1 | 0.1 |
| | sodium chloride | 0.4 | 0.4 | 0.4 | 0.4 | 0.4 | 0.4 | 0.4 |
| | potassium hydroxide (adjust pH to 3.7) | q.s. | q.s. | q.s. | q.s. | q.s. | q.s. | q.s. |
| | purified water | balance | balance | balance | balance | balance | balance | balance |
| total | | 100 | 100 | 100 | 100 | 100 | 100 | 100 |
| (B)/(A) | | 0.024 | 0 | 0 | — | — | — | 0.024 |
| (B)/(C) | | 0.094 | 0.000 | 0.000 | — | — | — | — |
| pH | | 3.7 | 3.7 | 3.7 | 3.7 | 3.7 | 3.7 | 3.7 |
| evaluation | quickness of lathering | 23 | 24 | 25 | 19 | 16 | 18 | 11 |
| | richness of foam volume | 24 | 25 | 25 | 18 | 17 | 14 | 11 |
| | lightness of foam quality | 23 | 24 | 24 | 18 | 12 | 17 | 10 |
| | ease of movement of finger during bubbling | 24 | 24 | 24 | 17 | 15 | 12 | 13 |
| | no slimy feel during rinsing | 24 | 25 | 25 | 16 | 12 | 18 | 16 |
| | favorable dissipation property during rinsing | 23 | 22 | 22 | 14 | 11 | 16 | 13 |
| | no residual feel after rinsing | 24 | 23 | 23 | 9 | 11 | 14 | 14 |

*1 ammonium polyoxyethylene (1) lauryl ether sulfate: ethylene oxide weight average addition mole number - 1
*2 sodium polyoxyethylene (2) lauryl ether sulfate: ethylene oxide weight average addition mole number - 2
*3 C-HPC (7): C-HPC represented by the above formula (1), in which substitution degree (k) of the cationized ethyleneoxy group was 0.3 and substitution degree (m) of the propyleneoxy group was 1.3 (obtained from the Preparation Example 7. Described in Table 4).
*4 C-HPC (8): C-HPC represented by the above formula (1), in which substitution degree (k) of the cationized ethyleneoxy group was 0.3 and substitution degree (m) of the propyleneoxy group was 1.8 (obtained from the Preparation Example 8. Described in Table 4).
*5 C-HPC (9): C-HPC represented by the above formula (1), in which substitution degree (k) of the cationized ethyleneoxy group was 0.3 and substitution degree (m) of the propyleneoxy group was 1.3 (obtained from the Preparation Example 9. Described in Table 4).
*6 C-HPC (10): C-HPC represented by the above formula (1), in which substitution degree (k) of the cationized ethyleneoxy group was 0.3 and substitution degree (m) of the propyleneoxy group was 2.0 (obtained from the Preparation Example 10. Described in Table 4).
*7 2-ethylhexyl glyceryl ether: derived from alcohol which has been converted from propylene trimer by oxo method.
*8 isodecyl glyceryl ether: derived from alcohol which has been converted from propylene trimer by oxo method.

TABLE 7-continued

*⁹ HPC (hydroxypropyl cellulose): product name "HPC-M" (manufacturer: Nippon Soda Co., Ltd.)
*¹⁰ C-HEC (cationized hydroxyethyl cellulose): product name "POISE C-80M" (manufacturer: manufactured by Kao Corporation)
*¹¹ cationized guar gum: JAGUAR C-13S (manufactured by Rhodia)
*¹² dimethyl polysiloxane emulsion: mixture of viscosity (10000 mm²/s)/(10 mm²/s) = 95/5, average particle diameter of 4.0 μm, dimethyl polysiloxane 60% by weight)

Examples 32 to 35

The aqueous hair cleansing agent having the composition to be described below was prepared according to a common method, and then evaluated. Meanwhile, the pH indicates the value measured at 25° C. after diluting each composition with water to 20 times by weight.

Example 32

Shampoo: pH 3.9

| (component) | |
|---|---|
| ammonium lauryl ether (1) sulfate | 12.5 (% by weight) |
| (manufactured by Kao Corporation: EMAL 125A) | |
| C-HPC (7) (Preparation Example 7) | 0.3 |
| lauryl hydroxy sultaine | 1.7 |
| (manufactured by Kao Corporation: AMPHITOL 20HD) | |
| lauric acid | 0.4 |
| (manufactured by Kao Corporation: LUNAC L-98) | |
| malic acid (50% solution) | 0.75 |
| isodecyl glyceryl ether | 1.7 |
| ethylene glycol distearyl | 1.6 |
| cationized guar gum | 0.3 |
| (manufactured by Rhodia: JAGUAR C-14S) | |
| dimethyl polysiloxane | 0.5 |
| polypropylene (7) glycol (molecular weight 420) | 0.1 |
| (manufactured by ADEKA CORPORATION: ADEKA CARPOL DL-30) | |
| dipotassium glycyrrhizinate | 0.1 |
| sodium benzoate | 0.1 |
| ethanol | 0.3 |
| sodium chloride | 0.4 |
| eucalyptus extract | 0.1 |
| chamomile extract | 0.05 |
| panthenol | 0.05 |
| silk extract | 0.05 |
| aloe extract | 0.05 |
| sea weed extract | 0.05 |
| orange oil | 0.05 |
| potassium hydroxide | q.s. (adjust pH to 3.7) |
| fragrance | trace amount |
| purified water | balance |

Shampoo of Example 32 was found to have favorable lathering and favorable foam quality even in damaged hair, ease of movement of hand or finger during bubbling, excellent foam dissipation property during hair washing, and suppressed residual feel during rinsing.

Example 33

Shampoo: pH 3.9

| (component) | |
|---|---|
| ammonium lauryl ether (1) sulfate | 12.5 (% by weight) |
| (manufactured by Kao Corporation: EMAL 125A) | |
| C-HPC (7) (Preparation Example 7) | 0.3 |
| isodecyl glyceryl ether | 1.7 |
| lauryl hydroxy sultaine | 1.0 |
| (manufactured by Kao Corporation: AMPHITOL 20HD) | |
| lauric acid amide propylbetaine | 0.8 |
| (manufactured by Kao Corporation: AMPHITOL 20AB) | |
| lauric acid | 0.4 |
| (manufactured by Kao Corporation: LUNAC L-98) | |
| malic acid (50% solution) | 0.75 |
| ethylene glycol distearyl | 1.6 |
| cationized cellulose | 0.3 |
| (manufactured by Kao Corporation: POISE M-80) | |
| polypropylene (7) glycol (molecular weight 420) | 0.1 |
| (manufactured by ADEKA CORPORATION: ADEKA CARPOL DL-30) | |
| dimethyl diallyl ammonium chloride•acrylamide copolymer liquid | 0.2 |
| (manufactured by Lubrizol Corporation: MERQUAT 550) | |
| dipotassium glycyrrhizinate | 0.1 |
| dimethyl polysiloxane | 0.3 |
| sodium benzoate | 0.1 |
| ethanol | 0.3 |
| sodium chloride | 0.4 |
| eucalyptus extract | 0.1 |
| chamomile extract | 0.05 |
| panthenol | 0.05 |
| silk extract | 0.05 |
| aloe extract | 0.05 |
| sea weed extract | 0.05 |
| orange oil | 0.05 |
| potassium hydroxide | q.s. (adjust pH to 3.7) |
| fragrance | trace amount |
| purified water | balance |

Shampoo of Example 33 was found to have favorable lathering and favorable foam quality even in damaged hair, ease of movement of hand or finger during bubbling, excellent foam dissipation property during hair washing, and suppressed residual feel during rinsing.

Example 34

Shampoo: pH 5.0

| (component) | |
|---|---|
| ammonium lauryl ether (1) sulfate | 12.5 (% by weight) |
| (manufactured by Kao Corporation: EMAL 125A) | |
| C-HPC (7) (Preparation Example 7) | 0.3 |
| isodecyl glyceryl ether | 1.7 |
| lauryl hydroxy sultaine | 1.7 |
| (manufactured by Kao Corporation: AMPHITOL 20HD) | |
| lauric acid | 0.4 |
| (manufactured by Kao Corporation: LUNAC L-98) | |
| malic acid (50% solution) | 0.2 |
| Zinc pyrithione | 1.0 |
| ethylene glycol distearyl | 1.6 |
| cationized cellulose | 0.3 |
| (manufactured by Kao Corporation: POISE M80) | |
| polypropylene (7) glycol (molecular weight 420) | 0.1 |
| (manufactured by ADEKA CORPORATION: ADEKA CARPOL DL-30) | |
| dipotassium glycyrrhizinate | 0.1 |
| dimethyl polysiloxane | 0.5 |
| sodium benzoate | 0.1 |
| ethanol | 0.3 |
| sodium chloride | 0.4 |
| potassium hydroxide | q.s. (adjust pH to 5.0) |
| fragrance | trace amount |
| purified water | balance |

Shampoo of Example 34 was found to have favorable lathering and favorable foam quality even in damaged hair, ease of movement of hand or finger during bubbling, excellent dissipation property during hair washing, and suppressed residual feel during rinsing.

Example 35

Shampoo

| (component) | |
|---|---|
| ammonium lauryl ether (1) sulfate | 12.5 (% by weight) |
| (manufactured by Kao Corporation: EMAL 125A) | |
| C-HPC (7) (Preparation Example 7) | 0.3 |
| isodecyl glyceryl ether | 1.7 |
| lauryl hydroxy sultaine | 1.7 |
| (manufactured by Kao Corporation: AMPHITOL 20HD) | |
| lauric acid | 0.4 |
| (manufactured by Kao Corporation: LUNAC L-98) | |
| malic acid (50% solution) | 0.75 |
| ethylene glycol distearyl | 1.6 |
| Piroctone olamine | 0.5 |
| (manufactured by Rhodia: OCTOPIROX) | |
| cationized guar gum | 0.3 |
| (manufactured by Rhodia: JAGUAR C-14S) | |
| PPG-7 | 0.1 |
| (manufactured by ADEKA CORPORATION: ADEKA CARPOL DL-30) | |
| dipotassium glycyrrhizinate | 0.1 |
| dimethyl polysiloxane | 0.5 |
| sodium benzoate | 0.1 |
| ethanol | 0.3 |
| sodium chloride | 0.4 |
| potassium hydroxide | q.s. (adjust pH to 3.7) |
| fragrance | trace amount |
| purified water | balance |

Shampoo of Example 35 was found to have favorable lathering and favorable foam quality even in damaged hair, ease of movement of hand or finger during bubbling, excellent foam dissipation property during hair washing, and suppressed residual feel during rinsing.

The invention claimed is:

1. A cleansing composition, comprising components (A), (B), (C), and (D):
   (A) an anionic surfactant,
   (B) a glyceryl ether having an alkyl group or alkenyl group with from 4 to 12 carbon atoms,
   (C) a cationized hydroxypropyl cellulose, and
   (D) water,
   wherein the cationized hydroxypropyl cellulose is of formula (1):

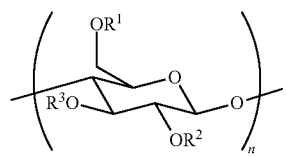

(1)

each of $R^1$, $R^2$ and $R^3$ is independently a group having a cationized ethyleneoxy group and a propyleneoxy group of formula (2) or (3):

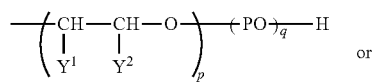

(2)

or

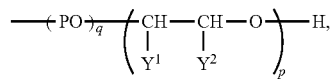

(3)

n, which is an average polymerization degree of anhydroglucose, is from 20 to 5000, an average mole number of the cationized ethyleneoxy group present in a molecule of the cationized hydroxypropyl cellulose per mole of anhydroglucose units is from 0.01 to 3, an average mole number of the propyleneoxy group present in a molecule of the cationized hydroxypropyl cellulose per mole of anhydroglucose units is from 0.01 to 5, in each of formula (2) and formula (3), one of $Y^1$ and $Y^2$ is a hydrogen atom and the other is a cationic group of formula (4):

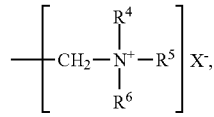

(4)

in each of formula (2) and formula (3), PO is a propyleneoxy group, p, a number of the cationized ethyleneoxy group (—CH($Y^1$)—CH($Y^2$)—O—) in formula (2) or (3), is 0 or 1, q, a number of the propyleneoxy group (—PO—) in formula (2) or (3), is from 0 to 4, when neither p nor q is 0, cationized ethyleneoxy groups and propyleneoxy groups may be arranged in any order, when p is 1 and q is 2 or higher, cationized ethyleneoxy groups and propyleneoxy groups may be arranged in blocks or randomly, in formula (4), each of $R^4$, $R^5$, and $R^6$ is independently a linear or branched alkyl group having from 1 to 3 carbon atoms, and $X^-$ is an anionic group.

2. A cleansing composition, comprising components (A), (B), (C), and (D):
   (A) from 3 to 40% by weight of an anionic surfactant,
   (B) from 0.01 to 5% by weight of a glyceryl ether having an alkyl group or alkenyl group with from 4 to 12 carbon atoms,
   (C) from 0.01 to 10% by weight of a cationized hydroxypropyl cellulose, and
   (D) water,
   wherein the cationized hydroxypropyl cellulose is of formula (1):

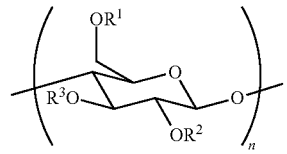

(1)

each of $R^1$, $R^2$ and $R^3$ is independently a group having a cationized ethyleneoxy group and a propyleneoxy group of formula (2) or (3):

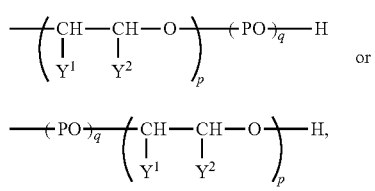

n, which is an average polymerization degree of anhydroglucose, is from 20 to 5000 an average mole number of the cationized ethyleneoxy group present in a molecule of the cationized hydroxypropyl cellulose per mole of anhydroglucose units is from 0.01 to 3, an average mole number of the propyleneoxy group present in a molecule of the cationized hydroxypropyl cellulose per mole of anhydroglucose units is from 0.01 to 5, or in each of formula (2) and formula (3), one of $Y^1$ and $Y^2$ is a hydrogen atom and the other is a cationic group of formula (4):

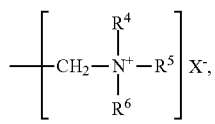

in each of formula (2) and formula (3), PO is a propyleneoxy group, p, a number of the cationized ethyleneoxy group (—CH($Y^1$)—CH($Y^2$)—O—) in formula (2) or (3), is 0 or 1 q, a number of the propyleneoxy group (—PO—) in formula (2) or (3), is from 0 to 4, when neither p nor q is 0, cationized ethyleneoxy groups and propyleneoxy groups may be arranged in any order, and when p is 1 and q is 2 or higher, cationized ethyleneoxy groups and propyleneoxy groups may be arranged in blocks or randomly, in formula (4), each of $R^4$, $R^5$, and $R^6$ is independently a linear or branched alkyl group having from 1 to 3 carbon atoms, and $X^-$ is an anionic group.

3. The cleansing composition according to claim 1, wherein a weight ratio between the components (B) and (C), (B)/(C), is from 0.2 to 6.

4. The cleansing composition according to claim 1, further comprising (E) a polymer other than the component (C).

5. The cleansing composition according to claim 4, wherein the polymer as the component (E) comprises at least one selected from the group consisting of (E1) a cationic polymer, (E2) an anionic polymer, (E3) a non-ionic polymer, and (E4) an amphoteric polymer.

6. The cleansing composition according to claim 5, wherein a weight ratio between the components (C) and (E1), (E1)/(C), is from 0.1 to 5.

7. The cleansing composition according to claim 1, which is a skin cleansing agent.

8. A method for washing skin, comprising applying the cleansing composition according to claim 1 to a skin of human body for cleansing, and then rinsing it.

9. An aqueous hair cleansing agent, comprising components (A), (B), (C), and (D):
(A) an anionic surfactant,
(B) a monoalkyl glyceryl ether or monoalkenyl glyceryl ether having an alkyl group with from 4 to 12 carbon atoms or an alkenyl group with from 4 to 12 carbon atoms,
(C) a cationized hydroxypropyl cellulose, and
(D) water,
wherein the cationized hydroxypropyl cellulose (C) has a main chain derived from anhydroglucose of formula (1):

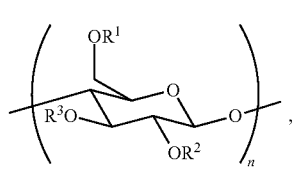

an average mole number of the cationized ethyleneoxy group present in a molecule of the cationized hydroxypropyl cellulose per mole of anhydroglucose units is from 0.01 to 2.9, an average mole number of the propyleneoxy group present in a molecule of the cationized hydroxypropyl cellulose per mole of anhydroglucose units is from 0.1 to 4.0, each of $R^1$, $R^2$ and $R^3$ is independently a group having the cationized ethyleneoxy group and the propyleneoxy group of formula (2):

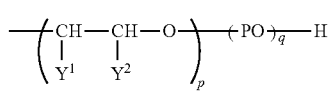

n, which is an average polymerization degree of anhydroglucose, is from 50 to 5000, in each of formula (2) and formula (3), one of $Y^1$ and $Y^2$ is a hydrogen atom and the other is a cationic group of formula (4):

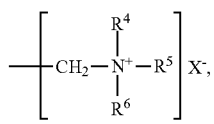

in each of formula (2) and formula (3), PO is a propyleneoxy group, p, a number of the cationized ethyleneoxy group (—CH($Y^1$)—CH($Y^2$)—O—) in formula (2), is 0 or 1 q, a number of the propyleneoxy group (—PO—) in formula (2), is from 0 to 4, p is not 0 for all $R^1$, $R^2$ and $R^3$, q is not o for all $R^1$, $R^2$, and $R^3$, when neither p nor q is 0, cationized ethyleneoxy groups and propyleneoxy groups may be arranged in any order, when p is 1 and q is 2 or higher, cationized ethyleneoxy groups and propyleneoxy groups may be arranged in blocks or randomly, in formula (4), each of $R^4$, $R^5$, and $R^6$ is independently a linear or branched alkyl group having 1 to 3 carbon atoms, and $X^-$ is an anionic group.

10. The aqueous hair cleansing agent according to claim 9, wherein a content of the component (C) is from 0.01 to 10% by weight relative to the total aqueous hair cleansing agent.

11. The aqueous hair cleansing agent according to claim 9, wherein a weight ratio of the component (C) to the component (A), (C)/(A), is from 0.0005 to 0.5.

12. The aqueous hair cleansing agent according to claim 9, wherein a weight ratio of the component (C) to the component (B), (C)/(B), is from 0.002 to 50.

13. The aqueous hair cleansing agent according to claim 9, wherein a content of the component (A) is 3 to 20% by weight relative to a total aqueous hair cleansing agent.

14. The aqueous hair cleansing agent according to claim 9, wherein a content of the component (B) is from 0.01 to 5% by weight relative to a total aqueous hair cleansing agent.

15. A method for washing hair, comprising applying the cleansing composition according to claim 9 to the hair for cleansing, and then rinsing it.

16. A method for washing hair, comprising applying the cleansing composition according to claim 9 to the hair, and then washing off it from the hair.

17. A method for washing skin, comprising applying the cleansing composition according to claim 2 to a skin of human body for cleansing, and then rinsing it.

18. A method for washing skin, comprising applying the cleansing composition according to claim 3 to a skin of human body for cleansing, and then rinsing it.

19. A method for washing skin, comprising applying the cleansing composition according to claim 4 to a skin of human body for cleansing, and then rinsing it.

20. A method for washing skin, comprising applying the cleansing composition according to claim 5 to a skin of human body for cleansing, and then rinsing it.

21. A method for washing skin, comprising applying the cleansing composition according to claim 6 to a skin of human body for cleansing, and then rinsing it.

22. A method for washing skin, comprising applying the cleansing composition according to claim 7 to a skin of human body for cleansing, and then rinsing it.

* * * * *